(12) United States Patent
Hickman et al.

(10) Patent No.: US 11,022,605 B2
(45) Date of Patent: Jun. 1, 2021

(54) MULTI-COMPONENT IN VITRO SYSTEM TO DEDUCE CELL SIGNALING PATHWAYS BY ELECTRONIC STIMULATION PATTERNS

(71) Applicant: University of Central Florida Research Foundation, Inc., Orlando, FL (US)

(72) Inventors: James Hickman, Orlando, FL (US); Lee Kumanchik, Orlando, FL (US); Navaneetha Santhanam, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 104 days.

(21) Appl. No.: 16/328,417

(22) PCT Filed: Aug. 16, 2017

(86) PCT No.: PCT/US2017/047085
§ 371 (c)(1),
(2) Date: Feb. 26, 2019

(87) PCT Pub. No.: WO2018/038987
PCT Pub. Date: Mar. 1, 2018

(65) Prior Publication Data
US 2019/0285616 A1    Sep. 19, 2019

Related U.S. Application Data

(60) Provisional application No. 62/379,892, filed on Aug. 26, 2016.

(51) Int. Cl.
*G01N 33/50*    (2006.01)
*C12M 1/34*    (2006.01)
(Continued)

(52) U.S. Cl.
CPC ......... *G01N 33/5014* (2013.01); *C12M 23/12* (2013.01); *C12M 41/46* (2013.01); *G01N 33/502* (2013.01); *G01N 33/5029* (2013.01)

(58) Field of Classification Search
None
See application file for complete search history.

(56) References Cited

U.S. PATENT DOCUMENTS 5,612,188 A    3/1997 Shuler et al.
8,815,584 B1   8/2014 Hickman et al.
(Continued)

OTHER PUBLICATIONS

Agarwal A, et al. Microfluidic heart on a chip for higher throughput pharmacological studies. Lab on a chip, d (2013).
(Continued)

*Primary Examiner* — Holly Kipouros
(74) *Attorney, Agent, or Firm* — Meunier Carlin & Curfman LLC

(57) ABSTRACT

Disclosed herein are cell culture analog devices, systems and methods for applying stimuli to components containing different cell types and recording the cell responses before, during, and after a stimulus (for example, a drug, metabolite, toxin, or electrical stimulus) is introduced. Responses can be stored to a database and compared to previous results. By analyzing how each cell type responds to various stimulation parameters, for example, by using multivariate analyses, cell signaling pathway information can be determined or new pathways can be discovered. In some implementations, an individual component interfaces with a specific cell type. This facilitates readout of the cell response to the stimulation. Various components can also interface with each other, such that the behavior of one cell type can affect a cell type in another component. Once assembled, the system is plugged into readout electronics and a programmable electrical stimulator.

30 Claims, 11 Drawing Sheets

(51) Int. Cl.
  *B01L 3/00* (2006.01)
  *C12M 1/32* (2006.01)

(56) References Cited

U.S. PATENT DOCUMENTS

| | | |
|---|---|---|
| 8,835,168 B2 | 9/2014 | Hickman et al. |
| 9,163,216 B1 | 10/2015 | Hickman et al. |
| 9,267,936 B2 | 2/2016 | Hickman et al. |
| 9,404,140 B1 | 8/2016 | Molnar et al. |
| 9,650,606 B2 | 5/2017 | Hickman et al. |
| 2003/0017445 A1 | 1/2003 | Berg et al. |
| 2003/0065452 A1 | 4/2003 | Hickman |
| 2003/0082795 A1 | 5/2003 | Shuler et al. |
| 2008/0132422 A1 | 6/2008 | Bohlen et al. |
| 2011/0250682 A1 | 10/2011 | Hickman et al. |
| 2012/0086679 A1 | 4/2012 | Goudar et al. |
| 2014/0206028 A1 | 7/2014 | Hickman et al. |
| 2014/0247971 A1* | 9/2014 | Bharadwaj ............ G06T 7/0012 382/133 |
| 2014/0274796 A1 | 9/2014 | Hickman |
| 2014/0278136 A1* | 9/2014 | Shamsheyeva .......... C12Q 1/18 702/19 |
| 2015/0219622 A1 | 8/2015 | Hickman et al. |
| 2015/0369791 A1 | 12/2015 | Hickman et al. |
| 2016/0041150 A1 | 2/2016 | Hickman et al. |
| 2016/0068812 A1 | 3/2016 | Hickman et al. |
| 2016/0305927 A1 | 10/2016 | Molnar et al. |
| 2017/0313980 A1 | 11/2017 | Hickman et al. |
| 2018/0095073 A1 | 4/2018 | Hickman et al. |

OTHER PUBLICATIONS

Ali HH, Utting JE, Gray C. Stimulus frequency in the detection of neuromuscular block in humans. Br J Anaesth 1970; 42:967-78.

Bellas E, et al. In vitro 3D full-thickness skin-equivalent tissue model using silk and collagen biomaterials, Macromolecular bioscience 12, 1627-1636 (2012).

Bers D M. Cardiac excitation-contraction coupling. Nature 2002; 415(6868): 198-205.

Carlsson L. In vitro and in vivo models for testing arrhythmogenesis in drugs. Journal of Internal Medicine 2006; 259(1): 70-80.

Dakhel Y. et al. Erythomycin potentiates pr interval prolonging effect of verapamil in the rat: A pharmacodynamic drug interaction. Toxicol Appl Phamacol 2006; 214: 24-29.

Das M, et al. A defined long-term in vitro tissue engineered model of neuromuscular junctions. Biomaterials 2010; 31: 4880-4888.

Das M, et al. Differentiation of skeletal muscle and integration of myotubes with silicon microstructures using serum-free medium and a synthetic silane substrate. Nature Protocols 2007; 2(7): 1795-1801.

Das M, et al. Electrophysiological and morphological characterization of rat embryonic motoneurons in a defined system. Biotechnology progress 19, 1756-1761, (2003).

Das M, et al, Embryonic motoneuron-skeletal muscle co-culture in a defined system. Neuroscience 2007; 146: 481-488.

Das M, et al. Long-term culture of embyonic rat cardiomyocytes on an organosilane surface in a serum free medium. Biomaterials 2004; 25(25): 5643-5647.

Das M, et al. Skeletal muscle tissue engineering: A maturation model promoting long-term survival of myotubes, structural development of the excitation-contraction coupling apparatus and neonatal myosin heavy chain expression. Biomaterials 30, 5392-5402 (2009).

Das M, et al. Temporal neurotransmitter conditioning restores the functional activity of adult spinal cord neurons in long-term culture. Experimental Neurology 2008; 209: 171-180.

Das, M. et al. A defined system to allow skeletal muscle differentiation and subsequent integration with silicon microstructures. Biomaterials 27, 4374-4380 (2006).

Davis, H. et al. Rat Cortical Oligodendrocyte-Embryonic Motoneuron Co-Culture: An Axon-Oligodendrocyte Interaction Model. Journal biomaterials tissue engin 2, 206-214 (2012).

Dhir V, et al. Patterning of diverse mammalian cell types in serum free medium with photoablation. Biotechnol Prog 2009; 25(2): 594-603.

Edwards D, et al. Addition of glutamate to serum-free culture promotes recovery of electrical activity in adult hippocampal neurons in vitro. J Neuroscience meth 190, 155-163 (2010).

Guo X F, et al. Characterization of a human fetal spinal cord stem cell line nsi-566rsc and its induction to functional motoneurons. Tissue Engineering and Regenerative Medicine 2010; 4: 181-193.

Guo X F, et al. Nmj formation between human stem cell derived motoneurons and rat skeletal muscle in a defined system. Tissue Engineering: Part C 2010; 16(6): 1347-1355.

Guo X, et al. Neuromuscular junction formation between human stern cell-derived motoneurons and human skeletal muscle in a defined system. Biomaterials 32, 9602-9611 (2011).

Guo X, et al. Derivation of sensory neurons and neural crest stem cells from human neural progenitor hNP1. Biomaterials 34, 4418-4427 (2013).

Hughes B. 2007 fda drug approvals: A year of flux specialty products dominate innovative drug approvals—a trend that looks set to continue. Nature Reviews Drug Discovery 2008; 7: 107-109.

Huh, D. et al. Reconstituting organ-levellung functions on a chip. Science 328, 1662-1668 (2010).

Jung D R, et al. Cell-based sensor microelectrode array characterized by imaging x-ray photoelectron spectroscopy, scanning electron microscopy, impedance measurements, and extracellular recordings. J VacSciTechnol A 1998; 16(3): 1183-1188.

Kang J H, et al. In vitro 3D model for human vascularized adipose tissue. Tissue Eng Part A 15, 2227-2236 (2009).

Kim C, et al. Non-cardiomyocytes influence the electrophysiological maturation of human embryonic stem cell-derived cardiomyocytes during differentiation. Stem cells and development 2010; 19(6): 783-795.

Kita-Matsuo H, et al. Lentiviral vectors and protocols for creation of stable hesc lines for fluorescent tracking and drug resistance selection of cardiomyocytes. Plos One 2009; 4(4): e5046.

Lawrence C L, et al. Nonclinical proarrhythmia models: Predicting torsades de pointes. Journal of Pharmacological and Toxicological Methods 2005; 52(1): 46-59.

Lipsett M A, et al. Acinar plasticity: development of a novel in vitro model to study human acinar-to-duct-to-islet differentiation. Pancreas 34, 452-457 (2007).

Liu W P, et al. Enantioselectivity in environmental safety of current chiral insecticides. Proc Natl Acad Sci USA 2005; 102(3): 701-706.

Lund A E, et al. Dose-dependent interaction of the pyrethroid isomers with sodium-channels of squid axon-membranes. Neurotoxicology 1982; 3(1): 11-24.

Maduell F. Hemodiafiltration. Hemodial Int 2005; 9(1): 47-55.

Mahler G J, et al. Characterization of a gastrointestinal tract microscale cell culture analog used to predict drug toxicity. Biotechnol Bioeng 2009; 104(1): 193-205.

Mahler G J, et al. Characterization of caco-2 and ht29-mtx co-cultures in an in vitro digestion/cell culture model used to predict iron bioavailability. J Nutr Biochem 2009; 20(7): 494-502.

Marona H R N, et al. Determination of sparfloxcin and its degradation products by hplc-pda. J Antimicrob Chemother 1999; 44: 301-302.

McAuliffe G J, et al. Developmentof a gastrointestinal tract microscale cell culture analog to predict drug transport. Mol Cell Bioengr 2008; 5(2): 119-132.

Meyer T, et al. Qt-screen: High-throughput cardiac safety pharmacology by extracellular electrophysiology on primary cardiac myocytes. Assay and Drug Development Technologies 2004; 2(5): 507-514.

Mohan D K, et al. Toxin detection based on action potential shape analysis using a realistic mathematical model of differentiated ng108-15 cells. Biosens Bioelectron 2006; 21: 1804-1811.

Molnar P, et al. Photolithographic patterning of c2c12 myotubes using vitronectin as growth substrate in serum-free medium. Biotechnol Prog 2007; 23(1): 265-268.

(56) References Cited

OTHER PUBLICATIONS

Molnar P, et al. Synaptic connectivity in engineered neuronal networks, in Patch-clamp methods and protocols, Molnar P and Hickman J J, Editors. 2007, Humana Press: New York.
Mufti N A, et al. Different in vitro systems affect cyp1a1 activity in response to 2,3,7,8-tetrachlorodibenzo-p-dioxin Toxicol in vitro 1998; 12: 259-272.
Nakamura Y, et al. The in vitro metabolism of a pyrethroid insecticide, permethrin, and its hydrolysis products in rats. Toxicol Appl Pharmacol 2007; 235: 176-184.
Natarajan A, et al. Engineered In Vitro Feed-Forward Networks. J Biotechnol Biomater 3, 2 (2013).
Natarajan A, et al. Microelectrode recordings of cardiac action potentials as a high throughput method to evaluate pesticide toxicity. Toxicol In Vitro 2006; 20(3): 375-381.
Natarajan, A. et al. Patterned cardiomyocytes on microelectrode arrays as a functional, high information content drug screening platform. Biomaterials 32, 4267-4274 (2011).
Oh T-i, et al. Real-time fluorescence detection of multiple microscale cell culture analog devices in situ. Cytometry Part A 2007; 71A: 857-865.
Pointer C, P et al. Ht29-mtx and caco-21tc7 monolayers as predictive models for human intestinal absorption: Role of mucus layer. J Pharm Sci 2001; 90: 1608-1619.
Rumsey J W, et al. Node of ranvier formation on motoneurons in vitro. Biomaterials 2009; 30: 3567-3572.
Rumsey J W, et al. Tissue engineering the mechanosensory circuit of the stretch reflex arc: Sensory neuron innervation of intrafusal muscle fibers. Biomaterials 31, 8218-8227 (2010).
Schaffner A E, et al. Investigation of the factors necessary for growth of hippocampal neurons in a defined system. J Neurosci Methods 1995; 62(1-2): 111-9.
Scollon E J, et al. In vitro metabolism of pyrethroid pesticides by rat and human hepatic microsomes and cytochrome p450 isoforms, Drug Metabolism and Disposition 2009; 37(1): 221-228.
Selivanova O M, et al. Compact globular structure of thermos thermophilus ribosomal protein s1 in solution. J Biol Chem 2003; 278(38): 36311-36314.
Sin A, et al. The design and fabrication of three-chamber microscale cell culture analog devices with integrated dissolved oxygen sensors. Biotechnol Prog 2004; 20: 338-345.
Subramanian, B. et al. Tissue-engineered three-dimensional in vitro models for normal and diseased kidney, Tissue Eng Part A 16, 2821-2831 (2010).
Sung J H, et al. A micro cell culture analog with 3-d hydrogel culture of multiple cell lines to assess metabolism-dependent cytotoxicity of anti-cancer drugs. Lab Chip 2009; 9(10): 1385-1394.
Sung J H, et al. A microfluidic device for a pharmacokinetic-pharmacodynamic (pk-pd) model on a chip. Lab Chip 2010; 10: 446-455.
Sung J H, et al. Fluorescence optical detection in situ for real time monitoring of enzymatic activity of liver cells in multiple microfludic devices. Biotechnol Bioeng 2009; 104: 516-525.
Sung J H, et al. Prevention of air bubble formation in a microfluidic perfusion cell culture system using a microscale bubble trap. Biomed Microdevices 2009; 11: 731-738.
Sung J H, et al. Micro-fabricated mammalian organ systems and their integration into models of whole animals and humans. Lab on a chip 13, 1201-4212 (2013).
Suter W. Predictive value of in vitro safety studies. Current Opinion in Chemical Biology 2006; 10(4): 362-366.
Sutton N M, et al Clinical effects and outcome of feline permethrin spot-on poisonings reported to the veterinary poisons information service (vpis), london. J Feline Med & Surgery 2007; 9: 335-339.
Swynghedauw B. Molecular mechanisms of myocardial remodeling. Physiol Rev 1999; 79(1): 215-262.
Takagishi Y, et al. Species-specific difference in distribution of voltage-gated 1-type ca2+ channels of cardiac myocytes. Am J Physiol Cell Physiol 2000; 279(6): C1963-1969.
Tatosian D A, et al. A novel system for evaluation of drug mixtures for potential efficacy in treating multidrug resistant cancers. Biotechnol Bioeng 2009; 103(1): 187-198.
van der Valk J, et al. Optimization of chemically defined cell culture media—replacing fetal bovine serum in mammalian in vitro methods. Toxicology in vitro: an international journal published in association with BIBRA 24, 1053-1063 (2010).
Varghese K, et al. A new target for amyloid beta toxicity validated by standard and high-throughput electrophysiology. PLoS One 2010; 5(1): e8643.
Varghese K, et al. Regeneration and characterization of adult mouse hippocampal neurons in a defined in vitro system. J Neurosci Methods 2009; 177: 51-59.
Viravaidya K, et al. Incorporation of 3t3-l1 cells to rmmic bioaccumulation in a microscale cell culture analog device for toxicity studies. Biotechnol Prog 2004; 20: 590-597.
Wagner, I, et al. A dynamic multi-organ-chip for long-term cultivation and substance testing proven by 3D human liver and skin tissue co-culture. Lab on a chip, 3538 (2013).
Wilson K, et al. Direct patterning of coplanar polyethylene glycol alkylsilane monolayers by deep-ultraviolet photolithography as a general method for high fidelity, long-term cell patterning and culture. JVST B 2011, 021020.
Wilson K, et al. Integration of functional myotubes with a bio-mems device for non-invasive interrogation. Lab Chip 2007; 7: 920-922.
Wilson. K, et al. Measurement of contractile stress generated by cultured muscle on silicon cantilevers. PLoS One 2010; 5(6): e11042.
Xu H, et al. Development of a stable dual cell-line gfp expression system to study estrogenic endocrine disruptors. Biotechnol Bioeng 2008; 101(6): 1276-1287.
Zimmermann W H, et al. Tissue engineering of a differentiated cardiac muscle construct. Circulation Research 2002; 90(2): 223-230.
International Search and Written Opinion in PCT/US2017/047805; dated Jan. 30, 2018.

* cited by examiner

MULTI-COMPONENT IN VITRO SYSTEM TO DEDUCE CELL SIGNALING PATHWAYS BY ELECTRONIC STIMULATION PATTERNS

CROSS REFERENCE TO RELATED APPLICATIONS

This application is a national stage application filed under 35 U.S.C. § 371 of PCT/US2017/047085, filed Aug. 16, 2017, which claims the benefit of U.S. Provisional Application No. 62/379,892, filed Aug. 26, 2016, and which is expressly incorporated herein by reference.

STATEMENT REGARDING FEDERALLY SPONSORED RESEARCH OR DEVELOPMENT

This invention was made with Government Support under Grant No. R01 NS050452 awarded by the National Institutes of Health and under Grant No. W81XWH-14-1-0162 awarded by the ARMY/MRMC. The Government has certain rights in the invention.

BACKGROUND

The major research uses of animals are both in assessing potential toxicity of chemicals and in drug testing. Animal tests often are long in duration, expensive, and raise ethical issues. Further, animal tests are not always predictive of human response. This fact is easily demonstrated in drug development where only 11% of chemicals exiting animal trials are successful in humans [Hughes 2007]. In terms of human response to environmental toxicants, it is not ethically possible to conduct direct tests on humans, and extrapolation of animal results to human response is problematic. Over-regulation results in unnecessary expense; under-regulation endangers human health and the environment, so better testing systems are necessary.

In vitro tests can supplement and may reduce dependency on animal tests. However, in vitro tests fail to capture many important aspects of human and mammalian response to chemicals. Most in vitro tests are based on the use of multi-well plates where isolated cells or tissues are placed in medium spiked with a bolus dose of the test chemical. Such systems miss key aspects of physiological response. For example, the dose dynamics in the body differ considerably from static systems as time-dependent changes in chemical concentration occur in the body at a tissue site due to the processes controlling absorption, distribution, metabolism and excretion of a compound. Further, static well systems typically use a single cell or tissue type; in the body, metabolites are exchanged between different tissue/organ compartments. Even if multiple tissue types were represented in a single well, the ratio of one tissue to another and the nature of the circuits connecting them can alter the time-dependent concentration of the metabolites. In addition to these factors, single cells in a well, in most cases, do not represent functional tissues or subsystems of the body, nor experience the mechanical forces the cells in the body do, particularly those associated with fluid flow, and these mechanical forces are known to alter gene expression and metabolism of many chemicals.

SUMMARY

Disclosed herein is a cell culture analog system for simulating the physiological condition of a living subject. The cell culture analog system includes a first chamber containing a first type of cell and a second chamber containing a second type of cell. The second chamber is in fluid connection with the first chamber. The cell culture analog system also includes a first sensor for non-invasively measuring a function of the first type of cell, a second sensor for non-invasively measuring a function of the second type of cell, and a computing device operably connected to the first sensor and the second sensor. The computing device is configured to receive data from at least one of the first sensor and the second sensor and apply a multivariate analysis to the data. The data include the function of at least one of the first type or the second type of cell. Examples of data include, but are not limited to, the frequency of a cellular action potential, the amplitude of a cellular action potential, the cellular contractile force, and/or the concentration of a biomarker. In some implementations, the multivariate analysis draws correlations between the data and biochemical pathways within the first type of cell, the second type of cell, or both.

In some implementations, the computing device is configured to access a database. The database can include information about how a stimulus affects biochemical pathways within the first type of cell, the second type of cell, or both. The computing device can be configured to store the data to the database, and it can be configured to recover a first set of data from the database for comparison to a second set of data.

Some implementations of the cell culture analog system include a third cell type. The first, second, and third cell types are selected from the group consisting of: cardiomyocytes, myotubes, liver cells, kidney cells, neurons, epithelial cells, or mucus-producing cells.

In some implementations, the first sensor is selected from the group consisting of a microcantilever, a microelectrode array (MEA), and a light sensor. In some implementations, the second sensor is selected from the group consisting of a microcantilever, a microelectrode array (MEA), and a light sensor.

In some implementations, the first type of cell is a muscle cell or neuron, the first sensor comprises an MEA and is configured to measure the electrical activity of the first type of cell, the second type of cell is cardiomyocyte or myotube, and the second sensor comprises a microcantilever in contact with the second type of cell and configured to deflect in response to force applied by the second type of cell.

Some implementations of the cell culture analog device include a third chamber containing a third type of cell and in fluid connection with the first and second chambers. The third type of cell can be a liver cell or a kidney cell.

In some implementations, the first type of cell is selected from the group consisting of a neuron, a cardiomyocyte, or a myotube. The first sensor can be a MEA or a microcantilever. A third type of cell may be included, the third type of cell being a liver cell or a kidney cell.

In some implementations, the first type of cell is a cardiomyocyte or a myotube, the first sensor is a microcantilever, and the first cell type is cultured on the first sensor. The first chamber further comprises a neuron cultured on the first sensor and forming a neuromuscular junction with the first cell type.

In some implementations, at least one of the first chamber or the second chamber has an inlet and an outlet for directing flow of a culture medium. A microfluidic channel can interconnect the first chamber and the second chamber. Some embodiments can include a plurality of fluidic channels interconnecting the first chamber and the second chamber, and an inlet and an outlet for re-circulation of a culture medium. The cell culture analog system can also include a pump configured to flow a culture medium through the first chamber and the second chamber.

Some implementations of the cell culture analog system can include a muscle-simulating component. The muscle-simulating component can include one or more microcantilevers having cardiomyocytes or myotubes cultured thereon. In some embodiments, the muscle-simulating component also includes a microelectrode array having cardiomyocytes or myotubes cultured thereon.

In some implementations of the cell culture analog system, the first chamber, the second chamber, the first sensor, and the second sensor are arranged on a chip. For example, the first chamber, the second chamber, the first sensor, and the second sensor can be arranged on the chip in a planar sequential relationship.

Some implementations include a stimulus generator operably connected to stimulation electrodes. The stimulation electrodes are in electrical contact with the at least one of the first type of cell or the second type of cell, and the stimulus generator is configured to apply a stimulus signal to the stimulation electrodes. The computing device can be operably connected to the stimulus generator and configured to vary a characteristic of the stimulus signal. For example, the stimulus signal can be at least one of amplitude or frequency. In some examples, varying a characteristic of the stimulus signal can include switching the frequency of the stimulus signal while maintaining the amplitude constant. Alternatively, varying a characteristic of the stimulus signal can include adjusting the amplitude of the stimulus signal while maintaining the frequency constant.

Some implementations of the cell culture analog system can include a recording device operably connected to the computing device and at least one of the first sensor or the second sensor. The recording device is configured to record data from at least one of the first sensor and the second sensor. In some implementations, a stimulus generator is operably connected to stimulation electrodes. The stimulation electrodes are in electrical contact with the at least one of the first type of cell or the second type of cell, and the stimulus generator is configured to apply a stimulus signal to the stimulation electrodes. The computing device is further configured to synchronize operations of the stimulus generator and the recording device. The computing device can be further configured to receive a timing signal from the stimulus generator, wherein operations of the stimulus generator and the recording device are synchronized based on the timing signal. The recording device can be, for example, a laser and a photodetector or an image capturing device.

A method for analyzing cell culture analog system data is also disclosed. The method includes receiving, at a computing device, data comprising a function of at least one of a first type of cell or a second type of cell; and applying a multivariate analysis to the data using the computing device. In some implementations, data including the function of the first type of cell is received from a first sensor for non-invasively measuring the function of the first type of cell. In some implementations, data including the function of the second type of cell is received from a second sensor for non-invasively measuring the function of the second type of cell. The data can include cellular action potential frequency, cellular action potential amplitude, cellular contractile force, or a combination thereof. Some implementations of the method can also include receiving, at the computing device, a concentration of a biomarker expressed by or excreted by the first type of cell or the second type of cell, wherein the concentration of the biomarker is included in the multivariate analysis. Some implementations can further include identifying a biochemical pathway associated with at least one of the first type of cell or the second type of cell using the multivariate analysis. The data can be stored to a database. Alternatively or in addition, a result of the multivariate analysis can be stored to the database. In some implementations, the computing device is used to retrieve database a previous set of data or a previous result of the multivariate analysis from the database.

Some implementations of the method include applying a stimulus to at least one of the first type of cell or the second type of cell. The stimulus can be at least one of the group consisting of a drug, a toxin, a metabolite, or an electrical stimulation. Application of the stimulus can be repeated. In some implementations, the period of time between repeated stimuli is at least 24 hours. The stimulus can be varied over time. The variation can affect at least one of the group consisting of: drug concentration, toxin concentration, metabolite concentration, electrical stimulation frequency, electrical stimulation pulse duration, or electrical stimulation amplitude. Data, including the function of the first type of cell and/or the second type of cell in response to the stimulus, can be received at the computing device while the stimulus is varied.

DESCRIPTION OF DRAWINGS

As seen in FIG. 2A, any number of modules can be combined and interconnected. Fluid for the entire network can be added or removed through the fluid access ports, for example when feeding cells or dosing with drugs. Additionally, flow only occurs via exchange between the fluid access ports. Therefore, modules or components with no flow can be made by restricting access to one access port. As seen in FIG. 2B, a single module can be made without flow by removing an access port and co-locating the other inside the module. As seen in FIG. 2C, a single module can be made with flow by adding the second access port. As seen in FIG. 2D, more modules allow more complex arrangements such as this three module network with branching interconnects.

As seen in FIG. 4A, a 4-layer housing is constructed including a single multi-electrode module. As seen in FIG. 4B, the 4-layer housing is combined to yield a micro cell culture analog device. As seen in FIG. 4C a 5-layer module is constructed that incorporates barrier tissue in a kidney model. In FIG. 4D, the 4-layer housing is depicted showing that the network topology can involve multiple levels.

In FIG. 5A, a single module no-flow housing is shown. In FIG. 5B, a single module flow housing is shown. In FIG. 5C, a five module flow housing is shown.

As shown in FIG. 9A, at high enough frequency an anomalous dip was observed. As shown in FIG. 9B, the dip frequency sensitivity was approximately exponential. This indicates two binding sites for curare.

FIG. 10A shows at high enough frequency an anomalous peak was observed. FIG. 10B shows that the peak frequency sensitivity followed a power trend.

DETAILED DESCRIPTION

Figure 1:
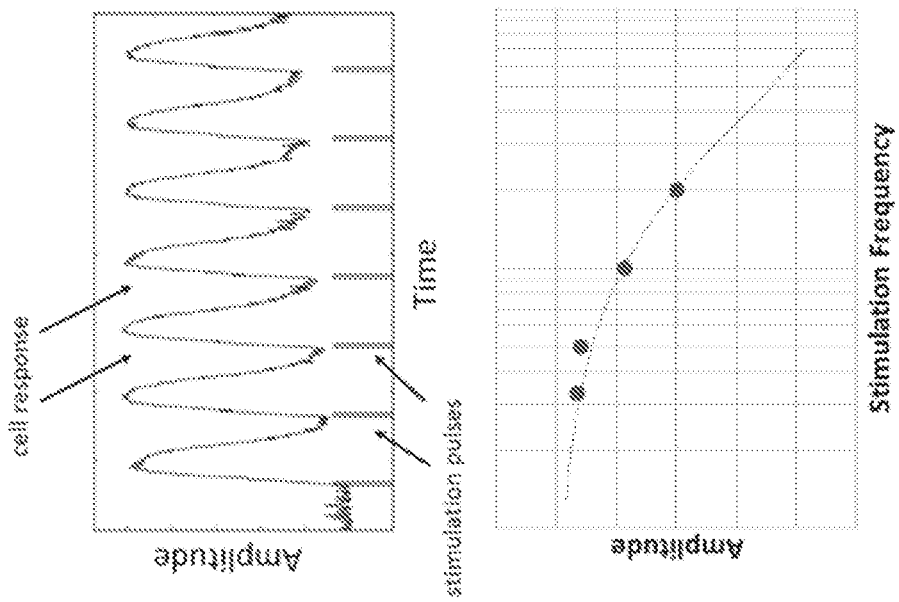
FIG. 1 shows the process flow. The flow chart on the left shows a computer signaling a stimulus generator to begin sending electrical pulses to cells contained in a component or module (or modules). Timing information is returned to the computer to synchronize with the readout electronics which record the cell responses. The plot at the right shows the analysis of the resulting data. Multiple stimulation patterns can be aggregated and observed to find pathway information.
Figure 1:
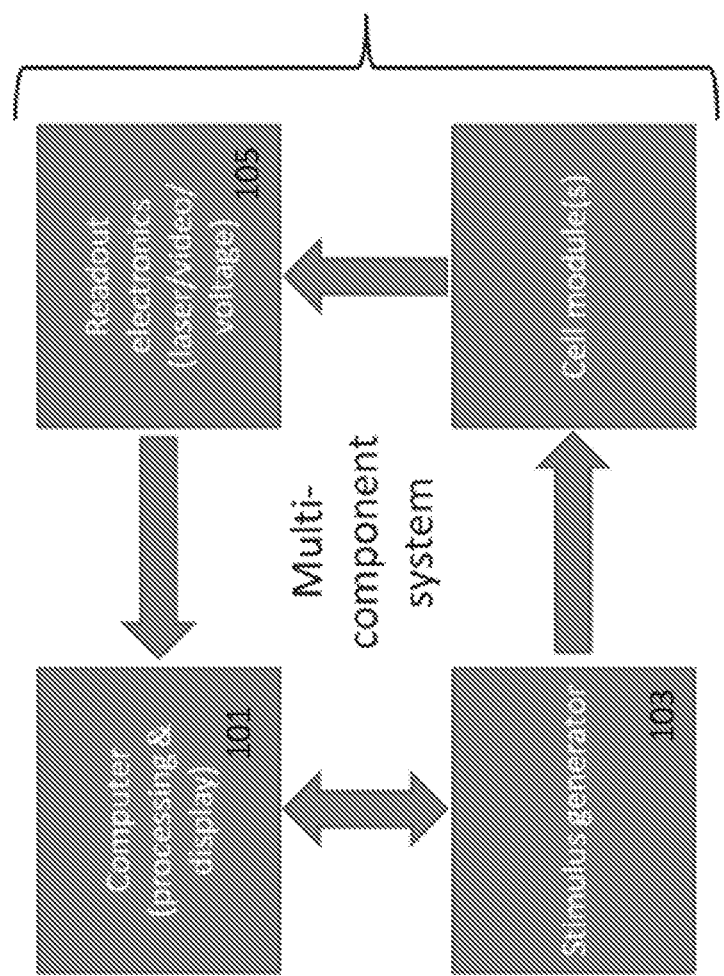

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

As used herein, the term "component" is interchangeable with the word "module".

Over time, cell culture medium has evolved from a simple salt solution to preserve tissue to more complex compositions, which can be used to maintain cells and tissues for extended periods of time. Human or animal sera, the most commonly used being fetal bovine serum, can be used to supplement basic media since they contain essential compounds for the growth and maintenance of cells.

To improve the quality, consistency and definition of the culture medium, serum free mediums can be used. Variations in mediums are known to affect cell culture maintenance and subsequent experimental data (Van der Valk et al., 2010). Serum-free media formulations can be based on the addition of cell-specific growth factors and supplements to a common base medium in order to facilitate the correct maintenance of specific cell cultures (Edwards et al., 2010). For example, following the first serum-free defined culture system for hippocampal neurons (Schaffner et al., 1995), a defined serum-free medium has been used with cardiomyocytes (Natarajan et al., 2011), motoneurons (Das et al., 2003), sensory neurons (Ramsey et al., 2010), and skeletal muscle cells (Das et al., 2006). In an aspect, in vitro cell-cultures can be designed to mimic the relevant in vivo environment. For example, a temperature of 37° C., and a controlled humidified gas mixture of 5% $CO_2$ and 95% $O_2$ can be used as the standard physical conditions. A blood surrogate medium with appropriate micro and macronutrients can be used to recreate the chemical milieu.

With respect to the disclosed systems, an advancement in the formulation of serum-free media was needed. These disclosed systems can maintain different cell types in a single housing; thus, it is a challenge to identify a common, serum-free formulation that can preserve functionality and morphological phenotypes of the different cells in co-culture. The need to maintain in vitro models for extended periods is of great importance for drug development applications. Assessment of chronic compound exposure to various tissues, and understanding the effects of prolonged metabolite or waste build-up in specific organ compartments can be essential for obtaining accurate predictions of in vivo responses to drug treatment.

Typical in vitro assessment of cell functionality and maturation within novel microdevices designed for drug development applications takes place over 1 to 2 weeks in culture. Such time frames have been employed for the assessment of a wide variety of in vitro analogues, including cardiac (Natarajan et al., 2011, Agarwal et al., 2013), lung (Huh et al., 2010), kidney (Subramanian et al, 2010), liver (Wagner et al., 2013), pancreas (Lipsett et al., 2007), skin (Bellas et al., 2012), fat (Kang et al., 2009) and neuronal (Natarajan et al., 2013) tissue models, with little information provided regarding more long-term survival. Longer in vitro culture periods tend to lead to cellular senescence or induction of apoptotic pathways, which can confound data analysis. While useful for a wide variety of basic biomolecular research, such timeframes are of more limited value for the study of chronic disease states and long term drug toxicity studies. Furthermore, when designing multi-organ systems for more accurate modeling of whole body responses (Sung et al., 2013), uniformity with regards to cell survival over extended time periods is preferable. An ability to maintain certain cells for 30 days in vitro is immaterial if other cells within the same culture platform begin to die after 14.

Longer culture periods have been established for certain cell types, and assessment of their development and functional maturation over such timeframes has been assessed. For example, skeletal muscle cultures have been shown to survive in vitro for up to 90 days, during which time they promote phenotype maturation, as evidenced by quantifiable changes in Myosin Heavy Chain isoform composition (Das et al., 2009). The systems disclosed herein can promote the long-term (30+ days) co-culture and functional interaction of skeletal muscle myotubes and motoneurons in defined conditions. The data provided herein demonstrate that maintenance of co-cultures is possible over longer periods provided careful consideration is given to culture variables such as surface, media formulation and correct temporal addition of exogenous stimuli.

The present disclosure comprises an in vitro model of biological living systems, such as animals or humans, for example, in response to chemicals or chemical mixtures. Such a model that mimics or simulates in vivo living biological systems reduces dependency on animal testing while providing improved predictions of responses of human or other organisms, such as plants, animals or insects. The present disclosure comprises micro cell culture analog (μCCA) methods, systems, and devices. These methods, systems and devices comprise microfabrication techniques, cell culture/tissue engineering and microfluidics. A CCA device, also referred to herein as "a cell culture analog system device," or a "component", is a physical representation of a physiologically-based pharmacokinetic (PBPK) model, and the functional in vitro systems reproduce in vivo effects of living tissues and organs, such as cardiac pacemaking, muscle dynamics, and neuronal information processing.

The present disclosure comprises cell culture analog systems comprising one or a plurality of components comprising cells grown in a microscale cell culture device, also referred to as a pCCA device, comprising one or more chambers or regions, wherein a component, along with cells contained therein a chamber or otherwise, and/or other elements, is analogous to a tissue, an organ or organ system. A component comprises a substrate for cells, such as a container for cells, a chamber, in which cells are contained, grown, acted on and/or maintained in the component. For example, a component may comprise, but is not limited to, a cardiac component comprising patterned biologically functional cardiac myocytes on microelectrode arrays. See U.S. patent application Ser. No. 12/938,701, which is incorporated by reference herein in its entirety for disclosing patterned rat cardiomyocyte cultures on microelectrode arrays in a serum-free medium for the study of cardiac physiology and pharmacology, utilizing a high-throughput technique.

Other example components can comprise a support substrate bearing a multielectrode array (MEA) and a negative surface resistant to cell attachment and deposited on the support substrate covering the MEA. The negative surface bears a pattern ablated on it by, for example, laser photolithography. A positive surface promoting cell attachment is deposited on the pattern ablated on the negative surface and cardiomyocytes adherent to the positive surface and growing aligned along the pattern. This application also teaches methods of making the culture of patterned cardiomyocytes. For example, a method comprises preparing a support substrate bearing a MEA, overlaying on the support substrate a negative surface resistant to cell adherence. The surface can comprise polyethylene glycol covering the MEA. Further, the method comprises ablating a pattern on the negative surface, depositing on the ablated pattern a positive surface promoting cell adherence and including fibronectin, adhering cardiomyocytes on the positive surface, and culturing the cardiomyocytes to grow on the positive patterned surface and align with the patterned surface.

A component can comprise more than one type of cell and may simulate organ systems which are comprised of more than one type of cell. Multicellular interactions, such as between the same cells and/or between different types of cells are included in the methods and compositions of the present disclosure. For example, muscle and neurons, which function in communication in a living body, may be provided in a single component and the cells may form neuromuscular junctions between the neurons and the muscle cells. Cells with genetic alterations may be used in methods and compositions of the present disclosure.

In an aspect, a component may comprise a muscular component comprising muscle cells. See U.S. patent application Ser. No. 12/765,399, which is incorporated by reference herein in its entirety for disclosing methods for lengthening the useful life of a culture of muscles cells by using disclosed mixtures of serum-free media, supplemented with growth factors.

In an aspect, a component can comprise a neural component. See U.S. patent application Ser. No. 12/117,339, which is incorporated by reference herein in its entirety for disclosing a method of culturing adult mammalian spinal cord neurons so that they exhibit electrical functionality.

In an aspect, a component can comprise a kidney-like filtering region, an "other tissues" region, and/or other regions analogous to body structures, organs or organ systems.

In an aspect, a cell culture analog system may comprise a hepatic component comprising liver cells, a gastrointestinal component comprising epithelial cells and/or mucus-producing cells. The present disclosure comprises methods for determining the effect of an input variable on a culture of cells, comprising contacting the cells of one or a plurality of components with an input variable and monitoring at least one output parameter. For example, a cell culture analog system may comprise a plurality of components comprising an hepatic (liver) component, a cardiac component, a motoneuron component, a kidney component, and/or a muscle component for testing compounds found in compositions that are commercially available, such as personal care compositions.

Also provided is micro cell culture analog system as disclosed herein, comprising one or a plurality of components, for example, comprising one or more of patterned biologically functional cardiac myocytes on microelectrode arrays, a hepatic component comprising liver cells, a gastrointestinal component comprising epithelial cells and/or mucus-producing cells, a muscular component comprising muscle cells, a kidney-like filtering component, an "other tissues region", a neural component, a neuromuscular component and/or other components analogous to body structures, organs or organ systems, and optionally, further comprising housing for enclosing the components or a board for immobilizing components. A component may comprise a first microscale chamber having a geometry simulating a first in vivo interaction with culture medium, wherein the first chamber comprises a first inlet and a first outlet for flow of the culture medium, and one or more channels coupled to the inlets and outlets of the chamber. An "any other tissues compartment" or "other tissues compartment" represents fluid hold-up or retention in non-adsorbing, non-metabolizing tissues which captures the dynamics of exposure to a chemical in the cell culture analog systems.

An aspect of the present disclosure comprises a component that mimics or simulates heart function in organisms, such as a human, animal or insect, comprising cardiac myocytes, surface embedded microelectrodes and patterned substrates on the microelectrode array to monitor the condition of the cardiac chamber in the IiCCA in real time and detect both acute and chronic functional toxic effects on the system.

Cultured cardiac myocytes are widely used in toxin detection and in drug development to screen for unwanted cardiac side effects [Meyer 2004]. Cardiac myocytes are useful whole-cell biosensors as they are spontaneously active, can be kept in culture in stable conditions for extended periods [Dhir 2009] and they respond to a wide spectrum of known and unknown toxins. Patterning cardiac myocytes on microelectrode arrays allows for the measurement of more advanced parameters, such as reverse use dependence, variability in QT interval and relative refractory periods [Natarajan 2011].

A cell culture analog system of the present disclosure comprises one or a plurality of components, which provide in vitro reproduction or simulation of a living body, with each component representing an organ or tissue in the living body. In a PBPK mathematical model, these chambers are interconnected in a manner analogous to blood flow in the body. In a CCA or component, the equations representing metabolism or adsorption in these chambers or compartments are replaced by living cells or tissues (e.g. liver, fat, lung, kidney, etc. all in the same device). Systems and devices of the present disclosure may be used for research, testing, diagnosis and insight into underlying biochemical mechanisms and how function is affected. By inserting functional tissues into components comprising mammalian cells or tissues, response from exposure to active agents, such as environmental chemicals, can be measured.

Components, systems and methods can be used with both animal cells and human cells, and non-animal cells such as insect or plant cells, and methods may comprise cross-species extrapolation. A basic concept of a iCCA has been demonstrated with studies on naphthalene toxicity [Sin 2004; Viravaidya 2004] on drug combinations to treat multidrug resistant cancer [Tatosain 2009] or colon cancer [Sung 2009] and, in preliminary studies, on hormone disruptors [Xu 2008]. The functional in vitro systems have been demonstrated for cardiac [Natarajan 2011; Natarajan 2006; Das 2004], neuronal [Jung 1998; Mohan 2006], muscle (Das 2007; Wilson 2007; Wilson 2010) and neuromuscular junction [Das 2010, Liu 2005] systems. See U.S. patent application Ser. No. 12/765,996, which is incorporated by reference herein in its entirety for disclosing long term in vitro cultures of tissue engineered functional neuromuscular junctions. See also U.S. patent application Ser. No. 13/102,672, which is incorporated by reference herein in its entirety for disclosing the formation of neuromuscular junctions in a defined system by co-culturing one or more human motor neuron cells and one or more rat muscle cells in a substantially serum-free medium.

The devices, systems and methods of the present disclosure comprise cells, including but not limited to, animal, human, plant or insect cells, and provide data that can reduce dependency on animals for testing and provides insights that cannot be obtained from whole animals. The disclosure can lead to a more accurate and cost-effective assessment of the toxicological potential of environment chemicals or chemical mixtures. Aspects of the present disclosure combine both "cell culture analogs" (CCA) with the development of functional tissue mimics. These approaches are combined to make a realistic in vitro model of a mammal and predict its response from exposure to a chemical or chemical mixture, referred to herein as an active agent, whether particularly active on a cell or not. The devices, systems and methods of the present disclosure may comprise systems for functional muscle as well as neuronal systems. The devices and methods may comprise use of human stem cells for more authentic constructs leading to a human based components, systems and methods.

The present disclosure comprises a physical representation of a physiological based pharmacokinetic (PBPK)

model. A PBPK model is a mathematical representation of the body, which treats the body as a set of interconnected compartments, each of which describes an organ or tissue. Each compartment is modeled as a chemical reactor, absorber, or surge tank. A set of reactive mass balances on parental compounds and metabolites are written for each compartment. Blood flow in and out of each compartment is simulated to match measured values. The model predicts the time dependent changes in the plasma and tissue compartment concentrations of parental compounds and metabolites. A person of skill would know that these mathematical models have been used in numerous studies on the toxicology of environmental chemicals.

While such computational models have proven to be useful aids in studies of absorption, distribution, metabolism, elimination, and toxicity (ADMET), they are limited. All relevant reactions and physiological responses are identified, particularly molecular mechanisms underlying cell response. For complex systems, such as mammals, it is difficult to capture not only the primary reactions but also all of the secondary responses (e.g., the metabolite of A, made in the liver, circulates to another tissue causing the release of B which then causes other cells to change physiologically). The disclosed components, arrays and methods compensate for this lack of knowledge.

In addition to the limitations of current in vitro tests to predict systemic effects, most assays are based on single cell analysis. It is well known that single cells are limited in their ability to mimic in vivo tissue function. Recently, functional cellular models, or multicellular systems that allow evaluation of properties previously only possible in intact animals or organs such as muscle dynamics [Wilson 2010], cardiac pacemaking [Natarajan 2011], neuronal function [Varghese 2010] and neuromuscular junction (NMJ) function [Guo 2010], have been developed to overcome these limitations but have not as yet been integrated. The disclosed components, arrays and methods provide a combination of these functional in vitro systems into a system that more accurately recapitulates the human response.

The components, systems and methods disclosed herein comprise physical replicas of a PBPK model with multiple types of mammalian cells cultured in a component instead of a mathematical description of the metabolism or absorption. Thus, the physiology of the cells compensates for lack of prior or incomplete knowledge. In an aspect, the fluid fraction feeding each component functions as the blood fraction received by the corresponding organ in vivo. Fluid is re-circulated just as in the body. Also, the fluid residence time, which describes the duration of cell-compound contact, in each component equals its in vivo value. For well-mixed systems, this residence time controls the amount of reaction. The liquid to cell ratio in each cell culture unit is managed to be as close as possible to its physiological value. Shear stress introduced by the flow is calculated and is kept at the physiological value for that type of tissue. Shuler described and constructed the first CCA and demonstrated its potential usefulness with naphthalene as a model toxicant in 1995. The initial device and several subsequent studies used bench scale systems. In later studies, the CCA's were constructed as microfabricated devices.

An advantage of the components, arrays (systems) and methods disclosed herein is that they are relatively inexpensive to make and can support high throughput studies. Further, the natural length scale (10 to 100 µm) is consistent with physiological length scales. Unlike other in vitro systems, such as multi-well plates, the disclosed components, systems and methods provide realistic dose dynamics (similar to what occurs in an animal or human) and allow for the formation and exchange of metabolites between compartments as well as exchange of compounds induced by the presence of the parental compound or metabolites. Coupling of the PBPK to the CCA and then to functional systems, as do the components, arrays (systems) and methods of the present disclosure is straightforward and can be used to test underlying molecular mechanisms.

Shuler has demonstrated the CCA concept with naphthalene (Sin 2004; Viravaidya 2004], showing that naphthaquinone (rather than naphthalene epoxide) was the reactive metabolite generated in the liver causing gluthathione depletion and loss of viability in the lung compartment. Subsequent studies examined the response to drug combinations. While animal studies are expensive with a single compound, such studies become even more difficult when chemical mixtures are to be tested. The combinations and permutations become large when several compounds are tested, particularly when each compound can involve multiple doses and when the order of exposure may be important. For example, the use of doxorubicin was tested with two multi-drug resistant (MDR) suppressing compounds (cyclosporine and nicardipine) for the treatment of MDR cancer [Tatosian 2009]; the action of the two MDR suppressors was found to be synergistic in the CCA, but this was not observable in multi-well plate assays. The use of Tegafur (a pro-drug for 5-flurouracil (5-FU)) and uracil combination treatment was examined for colon cancer using both a PK-PD model and a iCCA [Sung 2009]. As observed in animal trials, the CCA predicted that a uracil to Tegafur ratio of 4 to 1 was optimal in maximizing the concentration of 5-FU in the tumor relative to that in the blood. Unlike multi-well plates, the system indicated that 5-FU must be produced in the liver and circulate to the tumor to kill cells and that uracil (which inhibits the enzyme dihydroprymidinedehydrogenase) enhances the toxicity of Tegafur.

Technical enhancements to the pCCA system such as bubble traps, use of human reporter cell lines, and techniques to image the system in near real time have been made. A further enhancement involves connecting this model of systemic circulation with a model of a barrier tissue that controls entry into the body. Models of the gastrointestinal (GI) tract to model response to oral absorption of chemicals and drugs have also been constructed.

These initial CCA studies have been done primarily with cell lines either as monolayers or embedded in hydrogels. Such unorganized cell systems often lack key enzymes at realistic levels, and the biological functionality of the tissue is not well represented. Further measurements have been based solely on optically accessible end points such as fluorescence (e.g., dye reaction with gluthathione, uptake of naturally fluorescent compounds, viability stains, or reporter proteins, such as GFP). The addition of biologically functional tissues, such as patterned cardiac myocytes integrated with microelectrode Arrays (MEAs), increases the information control and allows for the use of electrical measurements to monitor response.

An aspect of the components, arrays and methods disclosed herein comprises using monitoring methods, which are 1) non-invasive, 2) more high throughput, 3) high information content, 4) functional, 5) able to detect known and unknown effects of active agents at physiological concentrations, 6) appropriate for continuous monitoring, 7) compatible with fluidic systems, and 8) mechanically robust. Hybrid (live-cell/electronic) systems have been developed to overcome several shortcomings of traditional whole-cell biosensors, at the same time preserving their advantageous properties over traditional physico-chemical or biochemical sensing methods.

Disclosed herein is a method which utilizes a cellular construct comprising cardiac myocytes, surface embedded microelectrodes and patterned substrates on the microelectrode array to monitor the condition of the cardiac chamber in a device of the present disclosure in real time. Cultured cardiac myocytes are widely used in toxin detection and in drug development to screen for unwanted cardiac side effects [Meyer 2004]. It has been shown that pyrethroids [Natarajan 2006] and heavy metals can be detected, and in some extent classified, based on their physiological effects on the spontaneous activity of cultured cardiac myocytes measured using a non-invasive, high-throughput, chronic protocol with substrate-embedded MEAs.

An aspect of the present disclosure comprises components, systems and methods comprising a "liver" analog region to mimic metabolism, a patterned cardiac myocyte/MEA functional reporter region, and an "other tissues" region, which is a compartment without any cells that represents the holdup of recirculating fluid in tissues where there is no adsorption or metabolism. For example, the methods disclosed herein allow for the validation of the integrated cardiac myocyte reporter region and the functional effects of stereoisomers of permethrin (a pyrethroid which is an environmental toxin) on the tissues in the system can be measured. Permethrin has four stereospecific isomers: 1R-cis-, 1R-trans-, 1S-cis-, and 1S-trans-. The 1R-cis- and 1R-trans-isomers are active, whereas the other two are not. Moreover, the cis isomers are about ten times more toxic than the trans isomers in vivo. Recent data indicated that the metabolic rate of cis-permethrin is much slower than that of the trans isoform, which could be an explanation for the different in vivo toxicity.

Disclosed herein are components, systems and methods that can be used to determine and measure the effect of different enantiomers, for example permethrin, on spontaneous beating and conduction velocity of patterned cardiac myocytes in the presence and absence of one or more chambers of a component representing the major metabolic pathways in the body. The lifetime of components can be extended to examine the effects of a compound in chronic studies.

The present disclosure comprises components, arrays and methods comprising patterned biologically functional cardiac myocytes on microelectrode arrays and other chambers comprising cells, structures, factors, co-factors or other elements for constructing analogs of organ tissues or systems that mimic physiological, physical, chemical, and/or electrical conditions of whole organisms.

The present disclosure comprises methods for determining the effect of an input variable on components, arrays and methods, comprising contacting cells comprised by one or more components with an input variable and monitoring at least one output parameter. For example, components, arrays and methods may comprise testing of active agents for beneficial or deleterious effects, long-term studies of exposure to active agents, determination of active metabolites or other studies designed by those skilled in the art using the components, arrays and methods disclosed herein.

The components and/or systems disclosed herein can comprise a housing for enclosing a component and/or systems disclosed herein, at least one component, wherein a component may be a microscale chamber having a geometry that simulates an in vivo interaction with culture medium, wherein the chamber comprises a first inlet and a first outlet for flow of the culture medium, and channels coupled to the inlets and outlets of the chamber. A component or system may be held in place or immobilized by attachment to or association with a board, a planar solid, to which the one or more components of a system are attached or associated.

The cell culture analog systems disclosed herein can comprise one or a plurality of components, wherein a component comprises a cardiac component, a neural component, a gastrointestinal component, a kidney-like component, an other tissues component or a hepatic component. A cell culture analog system comprises a cell culture analog system comprising a cardiac component and a hepatic component. A system comprises a cell culture analog system comprising a plurality of components comprising a cardiac component, a neural component and a hepatic component. A cell culture analog system comprises a cell culture analog system comprising a plurality of components comprising a cardiac component, a neural component, a gastrointestinal component, and a hepatic component. A cell culture analog system comprises a cell culture analog system comprising a plurality of components comprising a cardiac component, a neural component, a gastrointestinal component, a kidney-like component, and a hepatic component. A cell culture analog system comprises a cell culture analog system comprising a plurality of components comprising a cardiac component, a neural component, a gastrointestinal component, a kidney-like component, an other tissues component, a neuromuscular component, a muscular component and a hepatic component. A cell culture analog system comprises a cell culture analog system comprising a plurality of components comprising a cardiac component, a neural component, a gastrointestinal component, a kidney-like component, an other tissues component, a neuromuscular component, a muscle component and a hepatic component. A cell culture analog system comprises a cell culture analog system comprising a plurality of components comprising a neural component, a gastrointestinal component, a kidney-like component, an other tissues component and a hepatic component. A cell culture analog system comprises a cell culture analog system comprising a plurality of components comprising a gastrointestinal component, a kidney-like component, an other tissues component and a hepatic component. A cell culture analog system comprises a cell culture analog system comprising a plurality of components comprising an other tissues component and a hepatic component. A cell culture analog system comprises a cell culture analog system comprising a plurality of components comprising a cardiac component, a gastrointestinal component, a kidney-like component, an other tissues component and a hepatic component. A cell culture analog system comprises a cell culture analog system comprising a plurality of components comprising a cardiac component, a kidney-like component, an other tissues component and a hepatic component. A cell culture analog system comprises a cell culture analog system comprising a plurality of components comprising a cardiac component, an other tissues component and a hepatic component. A cell culture analog system comprises a cell culture analog system comprising a plurality of components comprising a cardiac component, and a gastrointestinal component. A cell culture analog system comprises a cell culture analog system comprising a plurality of components comprising a cardiac component, and a kidney-like component. A cell culture analog system comprises a cell culture analog system comprising a plurality of components comprising a cardiac component, a neuromuscular component, a muscle component and a hepatic component. An aspect of the present disclosure comprises a cell culture analog system comprising one component, two components, three components, four components, five components, six components, seven components, eight components, or more than eight components.

Disclosed herein are methods, systems and means for dynamically controlling a cell culture analog system, for example, comprising a computer (e.g., the example computing device of FIG. 11) and other elements, such as processors, sensors, actuators, etc., wherein, in an aspect, a method comprises analyzing data from a plurality of sensors to measure physiological events in one or more chambers of one or more components disclosed herein; optionally, regulating a cell culture characteristic such as temperature, light, oxygen, carbon dioxide, and/or fluid flow rates of a culture medium in at least one chamber of a component; and detecting biological or toxicological reactions in the cells or other elements of one or more chambers of a component: and optionally, upon detection, recording the change and/or changing one or more pharmacokinetic parameters of a component.

The devices, systems, and methods disclosed herein can comprise a computer-readable medium having computer-executable instructions stored thereon to perform a method. For example, a method may comprise analyzing data from a plurality of sensors to measure physiological events in one or more chambers of one or more components disclosed herein; optionally, regulating a characteristic such as temperature, light, oxygen, carbon dioxide, and/or fluid flow rates of a culture medium in at least one chamber of a component; and detecting biological or toxicological reactions in the cells or other elements of one or more chambers of a component; and optionally, upon detection, recording the change and/or changing one or more pharmacokinetic parameters of component.

An aspect of a cell culture analog system comprises the arrangement of the components in a system. A component may be in fluid connection with one or more components or conduits for fluid connection. A component may be a defined area or void in a solid material (for example, a silicone layer), such as a chamber formed by removal of a portion of the solid material to form an indentation or well in the solid material, such as the wells connected by fluid connections or channels formed in a solid material.

An aspect of a system of the present disclosure may comprise placing one or more components or portions of components on a platform that is capable of movement. In an aspect, a movable platform can allow gravity to affect or to drive fluid flow. For example, the component may be tilted. A method of the present disclosure may comprise tilting or moving a component from a position substantially parallel to a particular reference location, such as the earth's surface, or to a position at an angle to the particular reference location, such as the earth's surface. The tilting motion may be a one time, intermittently or constantly occurring for the component and/or system. A system or component of the present disclosure may comprise a movable stage that moves a cell culture analog system or component from a first position relative to a reference point to at least one different position, and may or may not return the system or component to the first position. For example, a system, component or method comprising a system and/or component may comprise a moveable platform on which a system or component is placed such that the system and/or component may be moved from a first position to at least one different position if movement is desired. A portion of a system or component may be configured to be moveable such that the portion may be moved from a first position to at least one different position if movement is desired. As used herein, tilting means moving a system or component of a system or a portion of a system or a component from a first position in three dimensional space to at least one different position in three dimensional space. A tilting action may include, but is not limited to, a one-time tilt wherein the system or component moves from one position to a second position; or may include tilting in a continuous or intermittent pattern between one or more positions other than the first position. Tilting may occur in a smooth, non-liner function. Tilting may be in a step function, for example, the system, component or portion thereof, may be moved from a first position to a one or more other positions, such as a tilt to a 10° position from the first position, pause at the second position, tilt to a 20° position from the first position, pause at the third position, tilt to a 30° position, pause at the fourth position, return tilt to a 20° position from the first position, pause at the third position, return tilt to a 10° position from the first position, pause at the second position, return to the first position, and optionally, repeat one or more times. Tilting may be in a single step function. For example, move the system or component quickly to +30° from the starting position, pause, move quickly to −30°, pause, back to +30°, and optionally, repeat one or more times.

An aspect of movement of a system or component or portion thereof comprises the time the system, component or portion thereof remains in one or more positions. Such time may be brief or long, from seconds to minutes to days to weeks, and may be determined by one of skill in the art, or may be used to mix compositions comprising media, cellular factors, cells, compounds to be tested, or other ingredients in a component or between components in a system. The period of movement of the system may be brief or long-term, and may be for seconds, minutes days or weeks, and may occur continuously from the start-up of a system or component to completion, or for one or more times during the use of the system or component, or may occur intermittently or randomly during the use of the system or component.

The movement of a system, component or portion thereof, may be uniform or non-uniform in any aspect, such as in time at a position, in time between movements, speed of the movement from one position to another, degree of tilt from the horizontal axis, number of cycles of movement from one position to one or more other positions, and combinations of these aspects. The amount and type of movement of a system, component or position thereof may be determined by keeping the flow rate constant to and between one or more components, a need to produce time-dependent flow rates or time dependent shear stresses, and/or to produce flow and movement to and between one or more components to mimic blood flow and conditions found in fluid dynamics in a living organism.

The devices, methods and systems disclosed herein can comprise in vitro methods and systems for mimicking the in vivo metabolism and response to stimuli of tissues, organs, organ systems of living organisms. One exemplary method includes determining the effect of an input variable on a simulated multi-organ system, comprising contacting at least one cell in a cell culture analog system which comprises a plurality of components, wherein a component comprises one or more chambers, chips or regions, and optionally, one or more types of cells; and one or more sensing elements, wherein one or more of the plurality of components is in fluid connection with another component, with an input variable and recording at least one output parameter. The method may comprise measuring and recording more than one output parameter, or a plurality of output parameters from a plurality of components. A step of recording at least one output parameter comprises obtaining information from a sensing element in a component.

A system may comprise a plurality of components of which at least one component is a cardiac-simulating component comprising cardiac cells cultured on one or more microcantilevers. A cardiac-simulating component may comprise cardiac cells cultured in a pattern on a microelectrode array with embedded microelectrodes. A system may comprise a plurality of components of which at least one component is a motoneuron component comprising neurons and myotubes forming neuromuscular junctions cultured on microcantilevers. A motoneuron component may comprise neurons and myotubes forming neuromuscular junctions cultured in a pattern on a microelectrode array with embedded microelectrodes. A system may comprise a plurality of components of which at least two component is a cardiac-simulating component and a motoneuron component. A component may comprise a tissue biopsy, such as ex plant tissue from a body, for example a dissected portion of a tissue or organ.

A cell culture analog system may further comprise connection elements, pumps, filters, sensors, alarms, and computer control elements. One or more components may be a microfluidic device. The cells may be derived from a human, an animal, a plant or an insect, or combinations and mixtures thereof. The cell culture analog system may further comprise serum-free culture medium.

A cell culture analog system may comprise at least a first component comprising a microscale chamber containing a first type of cell under conditions where the first type of cell provides at least one pharmacokinetic parameter value comparable to a value obtained for the same type of cell in vivo, wherein the first chamber comprises a first inlet and a first outlet for flow of culture medium; and comprises, a second component comprising a microscale chamber containing a second type of cell under conditions where the second type of cell provides at least one pharmacokinetic parameter value comparable to a value obtained for the same type of cell in vivo, wherein the second chamber comprises a second inlet and a second outlet for flow of culture medium; and a microfluidic channel interconnecting the first and second chambers. At least one component may comprise a first chamber comprising a first cell type maintained under conditions providing at least one pharmacokinetic parameter value comparable to values obtained for the cells in vivo; a second component comprises a second chamber of the same or different geometry than the first chamber comprising a second cell type maintained under conditions providing at least one pharmacokinetic parameter value comparable to values obtained for the cells in vivo; wherein the first and second chambers are interconnected by fluidic channels: and an inlet and outlet for re-circulation of culture medium.

In a method for testing the response(s) of a cell culture analog system to an input variable, an input variable may be an organic or inorganic chemical compound. An input variable may be more than one compound, and may be a mixture of inorganic and organic compounds. An input variable be may a pharmaceutical composition, an environmental sample, a nutritional sample, or a consumer product. An input variable may be a virus, liposome, nanoparticle, biodegradable polymer, radiolabeled particle or toxin, biomolecule, toxin-conjugated particle or biomolecule. The time period for testing the reaction of one or a plurality of components in a cell culture analog system may be for 72 hours, 84 hours, 96 hours, 108 hours, 120 hours, 132 hours, 144 hours, 156 hours, 168 hours, 180 hours, or for days or weeks, or longer, or any amount of time in between.

The cell culture analog systems disclosed herein can comprise a plurality of components, wherein a component comprises one or more chambers, chips or regions, and one or more types of cells; and one or more sensing elements, wherein one or more of the plurality of components is in fluid connection with another component. The system may further comprise connection elements, pumps, filters, sensors, alarms, and computer control elements. A component of the system may be a microfluidic device. The cells of the components of the system may be derived from a human, an animal, a plant or an insect, or combinations and mixtures thereof. At least one component may comprise a chip comprising biological cells on a microelectrode array comprising surface embedded microelectrodes. A cell culture analog system comprises at least one serum-free fluid culture medium.

A cell culture analog system may comprise at least one component comprising at least a first microscale chamber containing a first type of cell under conditions where the first type of cell provides at least one pharmacokinetic parameter value comparable to a value obtained for the same type of cell in vivo, wherein the first chamber comprises a first inlet and a first outlet for flow of culture medium: and optionally comprises, a second component comprising a second microscale chamber containing a second type of cell under conditions where the second type of cell provides at least one pharmacokinetic parameter value comparable to a value obtained for the same type of cell in vivo, wherein the second chamber comprises a second inlet and a second outlet for flow of culture medium; and a microfluidic channel interconnecting the first and second chambers. A cell culture analog system may comprise at least one component comprising a first chamber comprising a first cell type maintained under conditions providing at least one pharmacokinetic parameter value comparable to values obtained for the cells in vivo: and a second component comprising a second chamber of the same or different geometry than the first chamber comprising a second cell type maintained under conditions providing at least one pharmacokinetic parameter value comparable to values obtained for the cells in vivo; wherein the first and second chambers are interconnected by fluidic channels; and an inlet and outlet for re-circulation of culture medium. A cell culture analog system may comprise one or more additional microscale chambers containing the same or different types of cells as in the first or optionally second chambers, under conditions where the additional cell provides at least one pharmacokinetic parameter value comparable to a value obtained for the same type of cell in vivo, wherein the one or more additional chambers comprise an inlet and outlet for flow of culture medium. A cell culture analog system may operate for 72 hours, 84 hours, 96 hours, 108 hours, 120 hours, 132 hours, 144 hours, 156 hours, 168 hours, 180 hours, or for days or weeks, or longer, or any amount of time in between.

A cell analog system may use one or more culture media. For example, the entire system may use one culture media, such as a serum-free media, and that media may be circulated to one or more of the components in fluid connection in the system. Individual media components, such as nutritional compounds or growth cell factors may be added in individual components, and may or may not be circulated to other components of the system. The cells in a component may be grown and develop to the desired stage or number of cells in a component using a particular culture media and then that component may be joined into a cell analog system in which a different culture media, such as a serum-free media, is circulated throughout the entire system. A cell analog system of the present disclosure may comprise use of one culture media in each connected component. A cell analog system of the present disclosure may comprise use of more than one culture media, at different times during the operation of the system, or in different individual components.

EXAMPLES

Cells respond to external stimuli using tightly regulated biochemical pathways. These pathways represent a chain of events that are initiated by a stimulus and lead to a particular response for the cell. For cells that are electrically activated, the stimulus, which is a voltage or ionic current, can be shaped in ways not possible for biochemical stimuli. For example, the stimulus can be applied in bursts, held constant, given different polarity, etc. Each applied pattern generates a unique cell response which can be the result of different pathway activation. These responses can be modulated if a disruption along the pathway changes the fate of the signaling chain. The type of cell and nature of the disruption determines to what extent the cell response changes. By observing the cell response from multiple stimulation patterns before and after the administration of drugs or toxins, pathway information can be discriminated.

This technique is used clinically to monitor the effect of muscle relaxants during surgery (Ali, 1970). Transdermal electrical stimulation of a peripheral nerve to the hand or face using a train of four identical pulses causes muscle contractions. The type of relaxant administered determines how the resulting contractions are modulated. Nondepolarizing blockers make contractions from each successive pulse fade or reduce in amplitude whereas a depolarizing blocker has two phases. First, the amplitude of each contraction is reduced by the same amount. Then, the contractions fade just like in the nondepolarizing case.

The monitoring of muscle relaxants using electrical stimulation is an in vivo example. In vitro devices that deliver electronic stimulation also exist, for example, the multi-electrode array and the patch clamp. These devices feature programmable electronic stimulation, but in practice the stimulation parameters are not varied to determine biochemical pathway information. These devices also have two critical limitations. First, they can only measure the electrical response of cells; they can't measure other parameters like contractile force/length change for biomechanical cells. And second, they only measure the output of a single culture of cells. This limits the type of biological model that can be used and more importantly, limits the total amount of data that can be collected. Since drugs/toxins/metabolites can have a varied effect on different cells, having a system capable of recording from multiple cell-types is critical to determining how the drug/toxin/metabolite affects the pathway.

Example 1

System. FIG. 1 shows an example of a system that records the cellular responses to electrical stimulation patterns. The recording process is shown as a flow chart. A computer 101 triggers a stimulus generator 103 to electrically probe cells contained in modules while readout electronics 105 pass the cell responses back to the computer. It should be understood that the computer can be the example computing device 1100 shown in FIG. 11. Alternatively or additionally, the stimulus generator 103 can optionally be stimulus generator (A-M Systems isolated pulse stimulator model 2100). The stimulus generator 103 can be operably connected to one or more stimulation electrodes respectively arranged in each of the one or more compartments described herein (e.g., the liver, kidney, and/or downstream compartments). Optionally, the stimulation electrodes can be bath electrodes as described herein with respect to Example 4. Alternatively or additionally, the cell responses can be recorded using a laser scanner and photodetector for detecting deflection of at least one microcantilever (e.g., as described with regard to FIG. 7 herein), piezoelectric materials for detecting deflection of at least one microcantilever (as described in U.S. patent application Ser. No. 14/821,675, filed Aug. 7, 2015, which is hereby incorporated by reference in its entirety), imaging devices (e.g., video) for detecting deflection of at least one microcantilever (e.g., as described with regard to FIG. 8 herein), and/or microelectrode arrays (e.g., as described with regard to FIG. 6 herein). The stimulus generator also passes timing information back to the computer to synchronize with the readout electronics. The responses to different stimulation patterns are aggregated for analysis of pathway information. In this disclosure, the modules are functional units that interface to the cells.

Example 2

Figure 2:
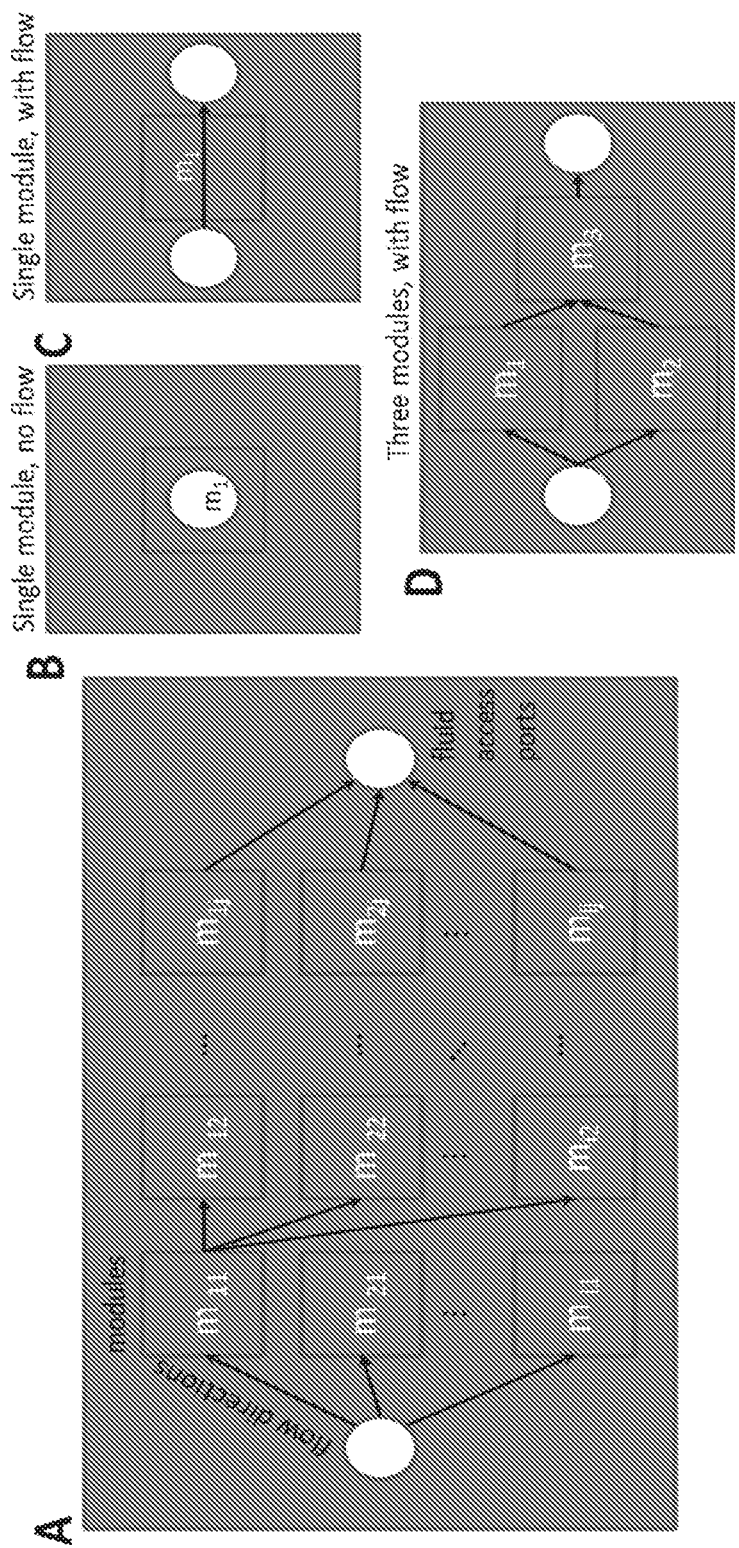
FIG. 2 shows the formation of a network formation by combining modules or components.

Components. FIG. 2 shows several schematics of networks formed by combining components, or modules, to represent a biological system of interest. Each component by itself is as simple as possible and complexity is added by interconnecting modules into a fluidic network. The network is designed by the user to simulate the physiology under study which in some cases, only requires a single module. At least one component or module within the network must receive electrical stimulation patterns. The network topology is shown in FIG. 2A. Any module within the path of both access ports will have flow which is important in certain physiological models. A no flow condition can be achieved by severing access to one port or removing a port all together, FIG. 2B. Flow modules with different network configurations are illustrated in FIG. 2C and FIG. 2D.

Figure 3:
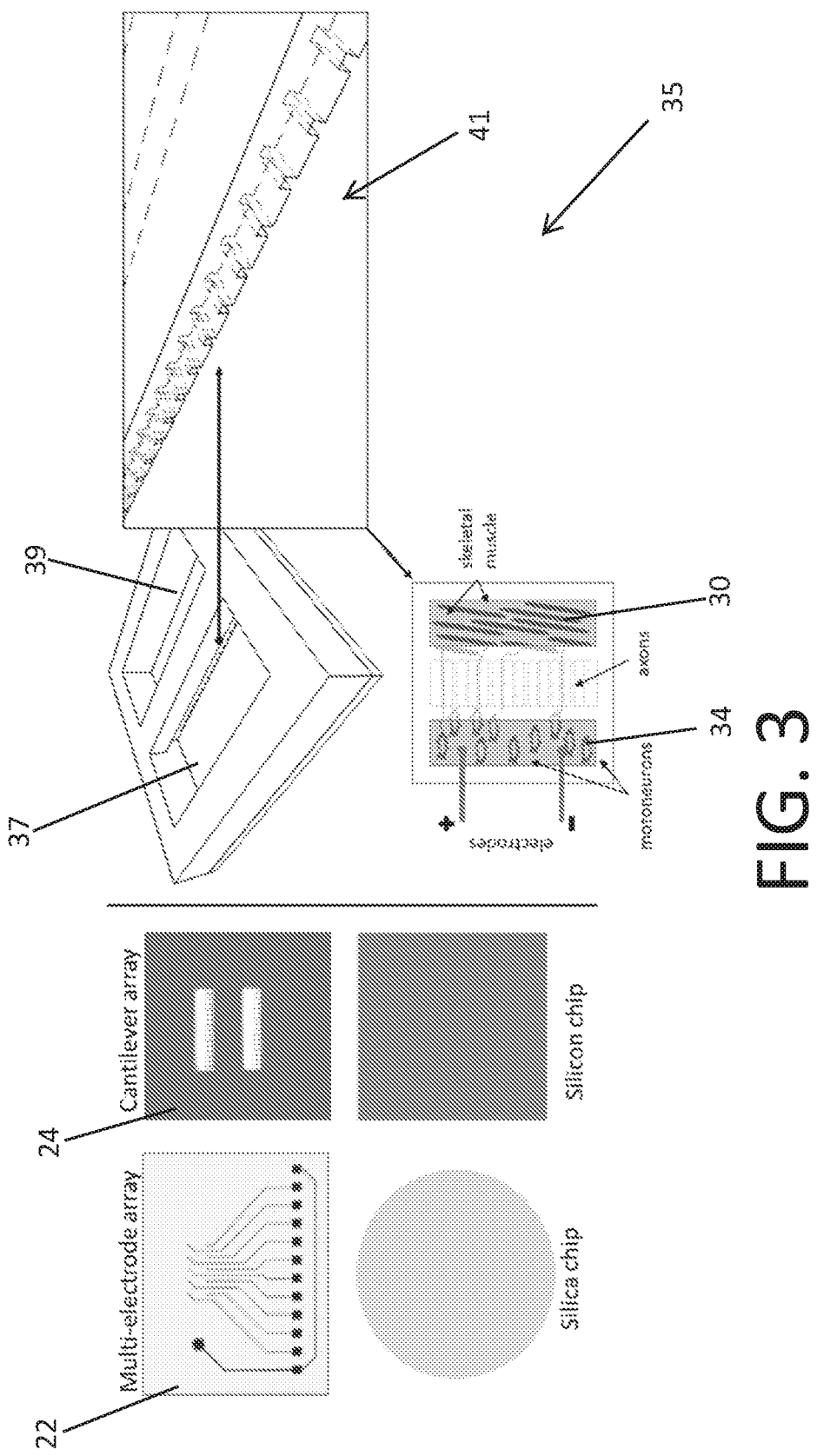
FIG. 3 shows that modules or components can have micro-chips which are specialized to interface with a specific cell-type and provide functional readout (micro-electrode array, cantilever array, micro-tunnel array). However, some chips are substrates for support cells that are added to a network to improve the physiological model.

Several components or modules use microchips which are shown in FIG. 3. The multi-electrode array 22 is a silica chip with patterned electrodes that interface with bioelectrical cells like neurons and cardiac muscle; it measures extracellular voltage levels. The cantilever array 24 is a silicon chip with micro-machined flexures that interface with biomechanical cells like skeletal and cardiac muscle; it measures force. The silica and silicon chips are generally used for cells that do not receive electrical stimulation patterns but are added to a network to achieve physiological relevance such as using a silica chip with liver cells to metabolize drugs. The micro-tunnel array 41 is a silicon chip with patterned silicone tunnels that interface neuronal cells 34 in one compartment with a target in the other. In this example, motoneurons innervate skeletal muscle cells 30 providing a neuromuscular junction model. Muscle contractions are measured by video.

Figure 4:
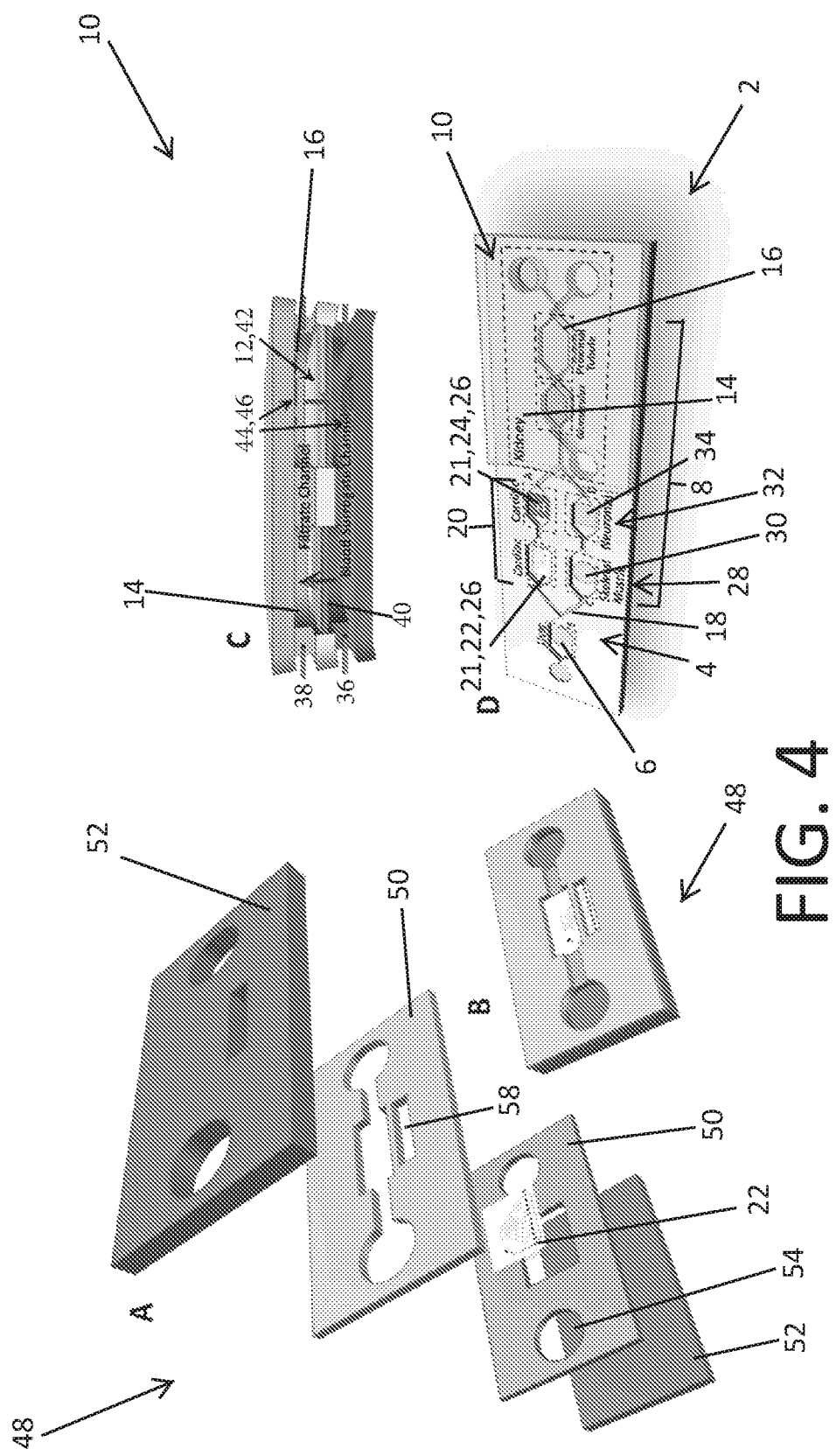
FIG. 4 shows networks of modules being realized using housings. These are created using multiple layers of plastic and silicone.

FIG. 4C depicts a kidney component 10 comprising a blood surrogate (media) channel 36 which comprises a flowing medium, a filtrate channel 38 comprising a flowing filtrate and positioned above the media channel, and a filtration system. The kidney component further comprises a glomerulus chamber 14 which promotes diffusive transport and a proximal tubule chamber 16 which promotes active transport. The glomerulus chamber in the example shown comprises a filter 40 which allows the diffusive passage of waste components that are below a certain size threshold.

The waste components passively flow from the media channel 36 side of the glomerulus chamber 14 to the filtrate channel 38 side of the glomerulus chamber. From there, they can be routed to a filtrate reservoir for further analysis, or they can be routed to the proximal tubule chamber 16. The proximal tubule chamber in the example shown has a proximal tubule cell culture 42 and electrodes 44, 46 of opposing polarity which facilitate the active transport of non-waste products through the proximal tubule cell culture. In this example, non-waste products are encouraged by an electric field to flow from the filtrate channel 38 back into the media (blood surrogate) channel 36. The flowing medium may then be routed to a media reservoir for further analysis, or it may be routed to another component of the micro cell culture analog system 2.

FIG. 4D shows a kidney component as part of a larger micro cell culture analog system 2. The entire system also includes a liver component 4, a cardiac component 20, a skeletal component 28, and a neuronal component 32. A flowing medium first contacts the liver component 4. The liver cell culture 6 of the liver component may produce certain waste products, i.e. metabolic products, when certain stimuli are being presented. The waste products from the liver component 4 then flow via connector conduits 18 to parallel cardiac and skeletal muscle components 20, 28, where the liver component waste products may have an effect on cardiac and/or skeletal muscle cell cultures 21, 30. The first cardiac component may, for example, comprise a microelectrode array 22 for recording action potentials and determining how the electrical properties of the cardiac cells have changed with the stimulus and with the waste products from the liver component. Another cardiac component may be placed in series, downstream from the first cardiac component. In this example, the second, downstream cardiac component can include a cantilever array 24 for measuring the mechanical response from a cardiac cell culture. Meanwhile, mechanical responses from the skeletal muscle component placed in parallel may also be measured, using a cantilever array. In the example shown in FIG. 4D, the media from the skeletal muscle component 28 then flows downstream to the neuronal component 32. The neuronal component 32 may include a microelectrode array for measuring the electrical responses to the waste-containing medium. Alternatively, a neuromuscular junction component 35 (shown in more detail in FIG. 3) may be used in place of the skeletal and neuronal components placed in series. As shown in FIG. 3, the neuromuscular junction component 35 can comprise a neuronal cell culture 34 cultured in a neuronal chamber 37 and on a microelectrode array 22, and positioned in fluid contact with a skeletal muscle cell culture 30 in a skeletal muscle chamber 39 and on a cantilever array 24. The skeletal muscle chamber and the neuronal chamber may be separated by a plurality of microtunnels 41, whereby axons can extend through the microtunnels to contact the skeletal muscles and form the neuromuscular junctions. Finally, as in the example shown in FIG. 4D, media from all of the upstream components can be combined and routed through a connector conduit 18 to the media channel 36 of the kidney component 10, which comprises the glomerulus chamber 14 and the proximal tubule chamber 16 and functions as described above in reference to FIG. 4C.

Example 3

Housings.

The components are interconnected inside housings 48 made by stacking layers of silicone and plastic 50, 52. A single-module with a multi-electrode array 22 inside a flow housing is illustrated in FIG. 4A. Here, the bottom and top layers are thick plastic layers 52 and the module compartment is made from two thin layers of silicone 50. Voids 54 in the silicone layers create the component chambers and the connector conduits. Collapsing the pieces together, except for the lid, shows the fluid path, FIG. 4B; the corded off area at the electrical interconnects is a dry chamber 58 and the lid has an opening to grant access to this area. More complex architectures are possible including multiple levels by stacking more layers of silicone and plastic as was done for the kidney module shown in FIG. 4C and FIG. 4D.

Figure 5:
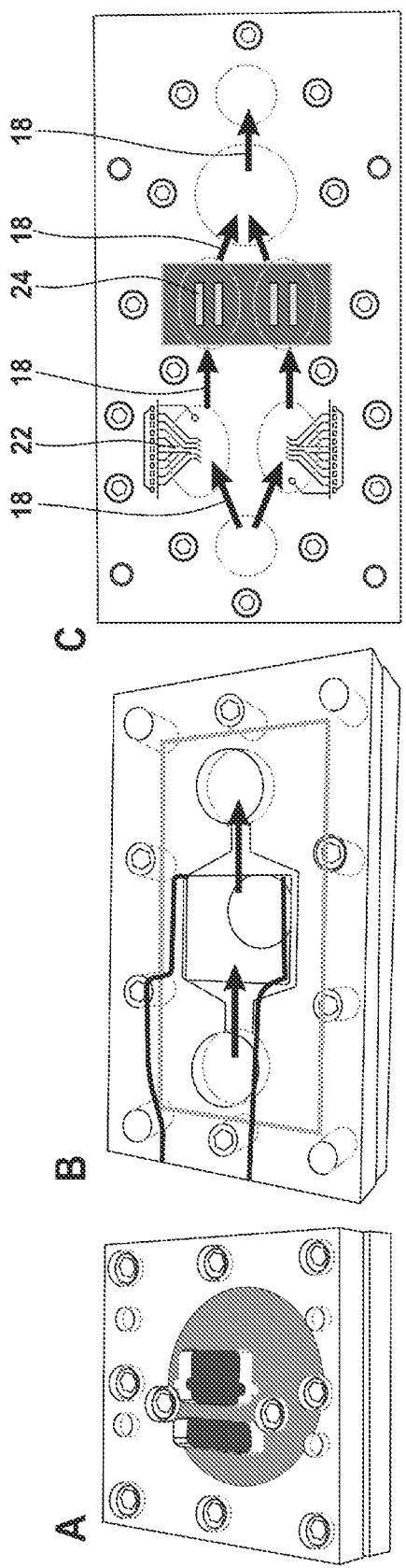
FIG. 5 shows prototypes of example housings.

Examples of housings are shown in FIG. 5. A single module housing with no flow has a single fluid access port right above the module chip, FIG. 5A. A single module housing with flow requires two fluid access ports connected to the module, FIG. 5B. A five component housing splits the flow between four components but recombines them at the fifth. The fifth component delivers liver metabolism for the whole network, FIG. 5C. The various components are interconnected by connector conduits 18, and in this example, some of the components include microelectrode arrays 22 and cantilever arrays 24.

Example 4

Stimulation and Readout.

Figure 6:
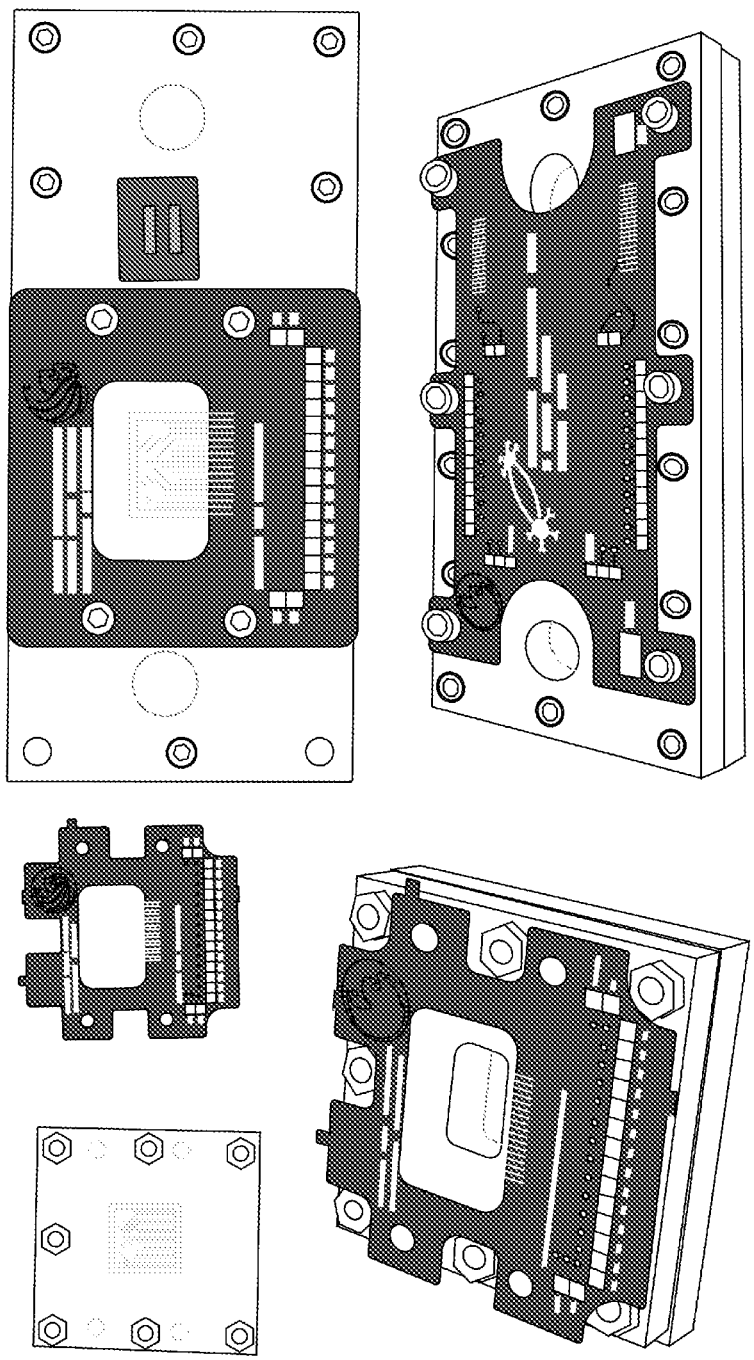
FIG. 6 shows an embodiment that includes printed circuit boards (PCB) for micro electrode arrays. In this embodiment, the PCB represents another layer of the housing. It makes contact with the chip inside through the dry opening in the housing. Pins or an elastomeric connector bridge the gap. An amplifier with spring loaded pins makes contact with the gold pads on the top of the PCB.
Figure 7:
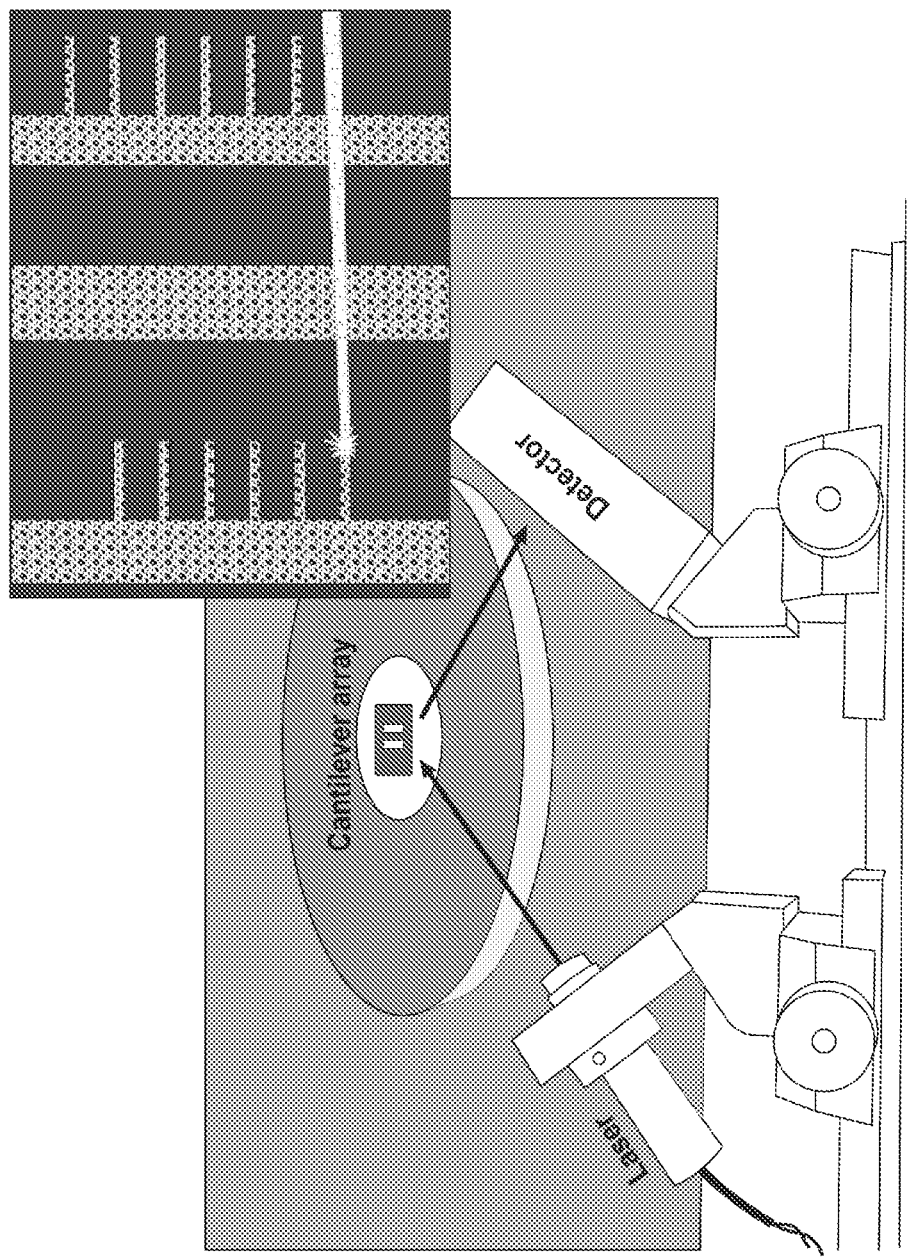
FIG. 7 shows a laser scanner for embodiments that include cantilever array chips. A laser bounced on the bottom of a cantilever with cells on top gets redirected to a photodetector. Contractions of the adhered cells cause flexing of the cantilever which redirects the laser across the detector.
Figure 8:
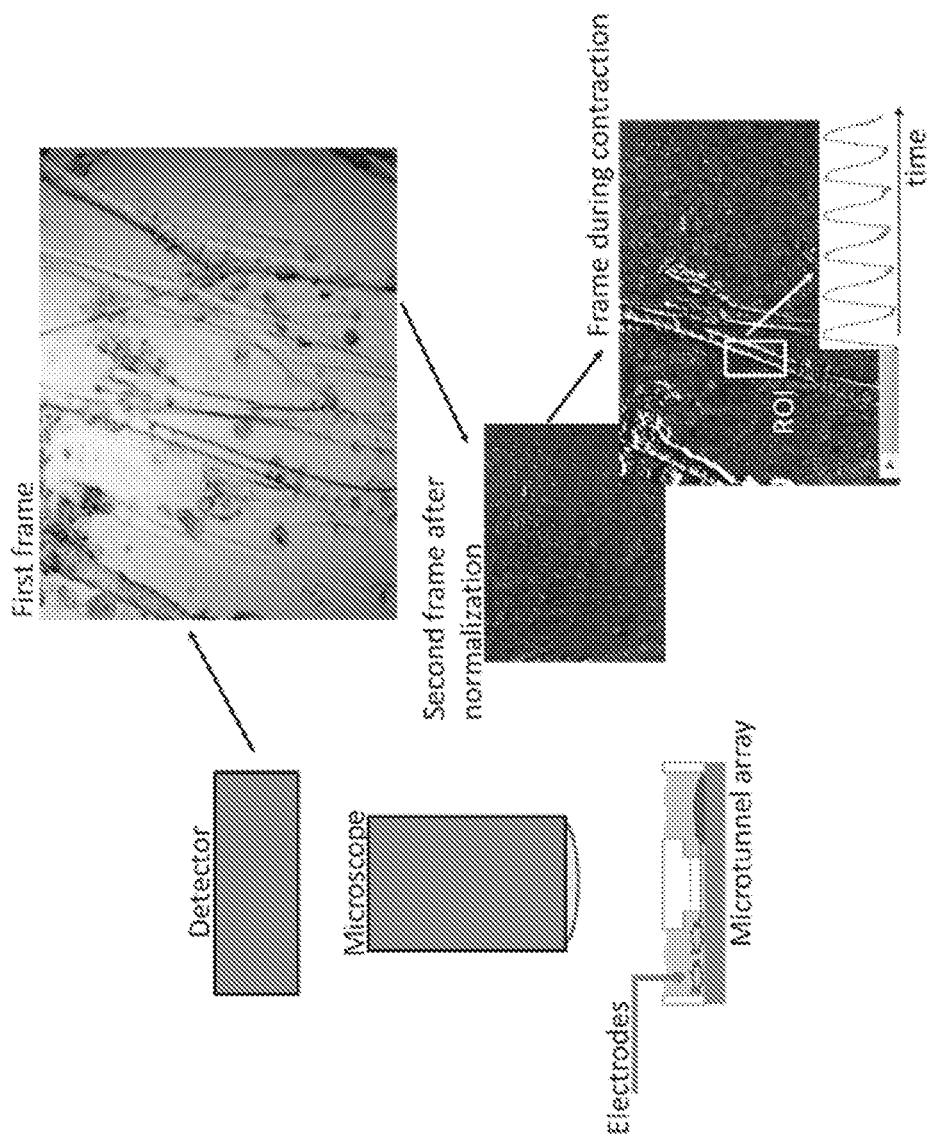
FIG. 8 shows video analysis of muscle movement in an embodiment including muscle cells. A microscope and camera observe a sample. A region of interest is selected where cells are moving. A pixel-by-pixel difference operation is performed on all frames in the video against the first frame. Movement produces a difference signal which is recorded.

Electronic interfacing for modules varies. In some embodiments, micro-electrode array chips are connected to a printed circuit board (PCB) which enables interfacing to a stimulus generator and amplifier, as shown in FIG. 6. The electrodes on the chip can perform both stimulation and readout. Cantilever arrays can use a laser scanner to readout biomechanical force from cells plated on the cantilevers, as shown in FIG. 7. Stimulation is applied through bath electrodes which are built into the module compartment inside the housing. Biomechanical cells can also be monitored by video to measure contractile motion, as shown in FIG. 8. Frames captured by the detector are normalized against the first frame. Movement by cells cause differences in these frames as compared to the first to become highlighted. By averaging the pixel intensity of a region of interest (ROI) where motion occurs, a plot of contractions versus time can be generated.

Example 5

Stimulation Patterns.

A voltage or current is injected into the stimulation electrodes present in each module while the cellular response is recorded. The stimulation is then varied. As described above, the stimulus (e.g., applied by the stimulus generator 101 of FIG. 1) can be applied in bursts, held constant, given different polarity, etc. For example, a fixed amplitude voltage is optionally pulsed at a given frequency for a period of time and then switched to another frequency for the same period of time. Alternatively, the amplitude can optionally be adjusted while the frequency is fixed. More complex patterns can be used such as bursts, like a train of four pulses. In some examples, the electrical stimulus can be repeated over the course of a lengthy period of time, for example, to study chronic conditions. For example, the stimulus could be applied repeatedly over the course of 28 days or more. In some examples, the stimulus might be spaced by a certain time duration. For example, a repeated stimulus might be spaced from the last stimulus by at least 24 hours. The goal is to record the responses to the various stimulation patterns. As described above, each applied pattern generates a unique cell response which can be the result of different pathway activation. These responses can be modulated if a disruption along the pathway changes the fate of the signaling chain. The type of cell and nature of the disruption determines to what extent the cell response changes. By observing the cell response from multiple stimulation patterns before and after the administration of drugs or toxins, pathway information can be discriminated.

Example 6

Drug Modulation.

Figure 9:
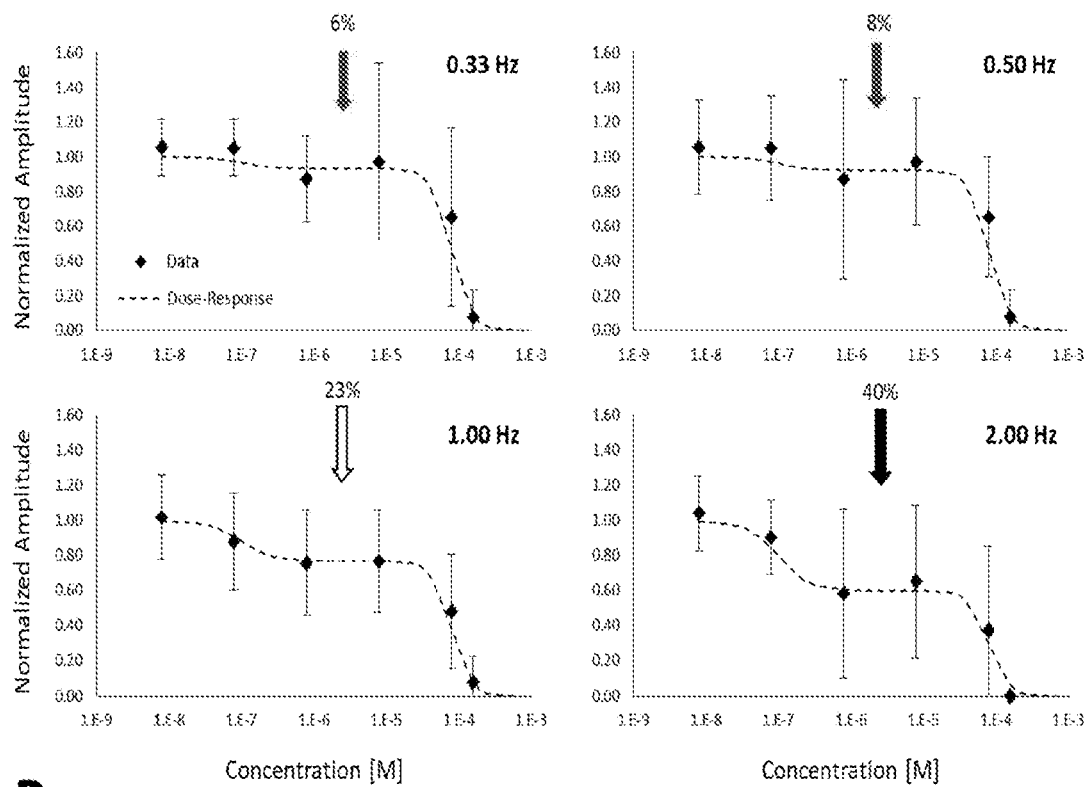
FIG. 9 shows the contractile response of skeletal muscle when a stimulation pattern was applied to synapsed motoneurons for varying concentrations of curare. The pattern chosen was repeated pulses at increasing frequency.
Figure 9:
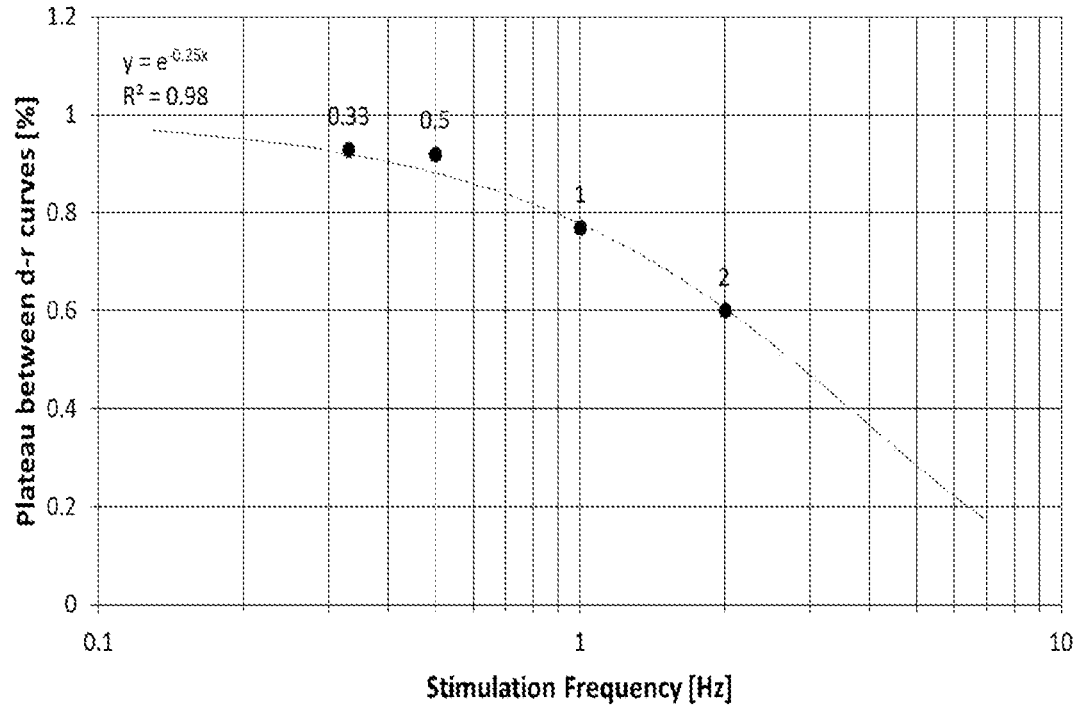

After a baseline is established, a drug can be added to the system. The stimulation pattern is repeated and differences in the cell response are noted. An example is illustrative. A neuromuscular junction model was set up using a single module with a microtunnel chip. The chip was plated with motoneurons on one side of the tunnels and skeletal muscle on the other side. Axons from the motoneurons traversed the barrier and synapse onto muscle. Bath electrodes were used to stimulate the motoneurons while the barrier prevented co-stimulation of the muscle. The stimulation caused depolarization of the motoneurons sending action potentials through the axons to the skeletal muscle. The resulting muscle contractions were recorded by video. The stimulation pattern was a bipolar, 50 ms pulse, fired at 0.33 Hz, 0.5 Hz, 1 Hz, and 2 Hz. Dose response curves were generated at each frequency for two drugs: curare and bungarotoxin, FIG. 9A and FIG. 10A, respectively.

For curare, the fitted parameters followed a biphasic curve, $$r(c) = \frac{1-p}{1+\left(\frac{c}{IC_{50_1}}\right)^{h_{c_1}}} + \frac{p}{1+\left(\frac{c}{IC_{50_2}}\right)^{h_{c_2}}}. \quad \text{Equation 1}$$

The biphasic curve means there are two concentrations for a half-maximum inhibitory response. These findings are in agreement with commonly reported results for acetylcholine receptors having two distinct binding locations for curare with different affinities. The effect is more prominent at higher frequency, where the plateau region shrinks exponentially for increasing frequency, FIG. 9B. In fact, at the lowest frequency, the effect is almost non-existent. The only way the effect presented itself was by stimulating at a high enough frequency showing the utility of the micro cell culture analog system.

The muscle response to increasing bungarotoxin concentrations followed a hermetic, biphasic dose-response, $$r(c) = p + \frac{1-p}{1+\left(\frac{c}{IC_{50_1}}\right)^{h_{c_1}}} + \frac{0-p}{1+\left(\frac{IC_{50_2}}{c}\right)^{h_{c_2}}} \quad \text{Equation 2}$$

Figure 10:
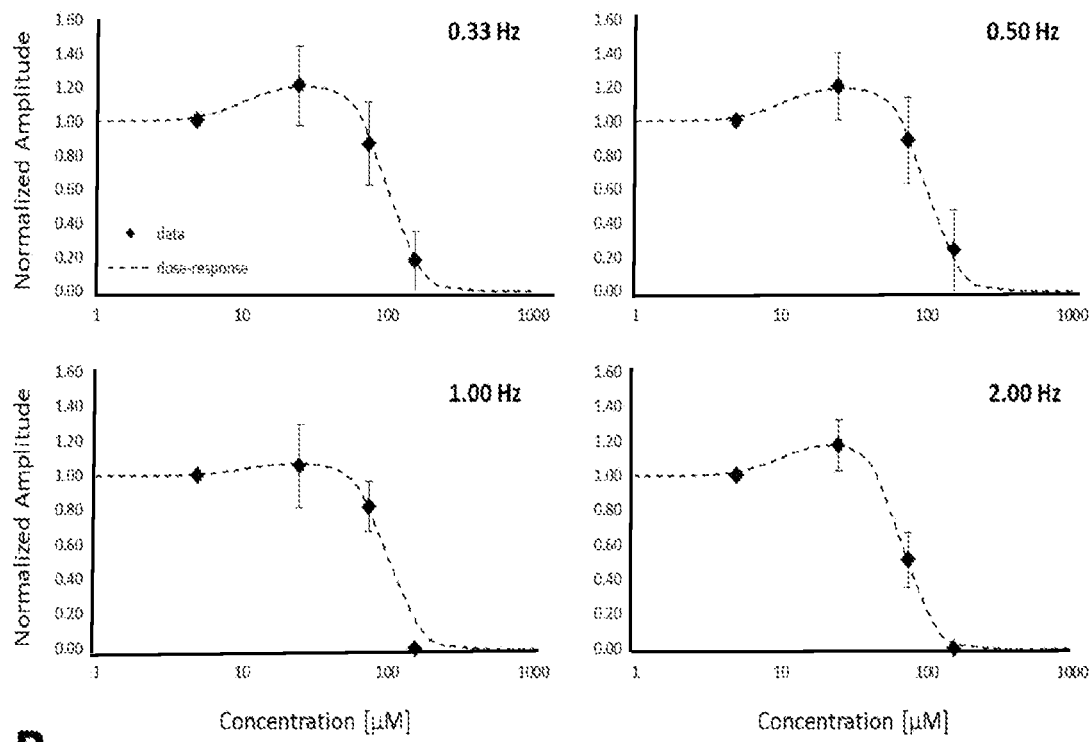
FIG. 10 shows the contractile response of skeletal muscle when a stimulation pattern was applied to synapsed motoneurons for varying concentrations of bungarotoxin. The pattern chosen was repeated pulses at increasing frequency.
Figure 10:
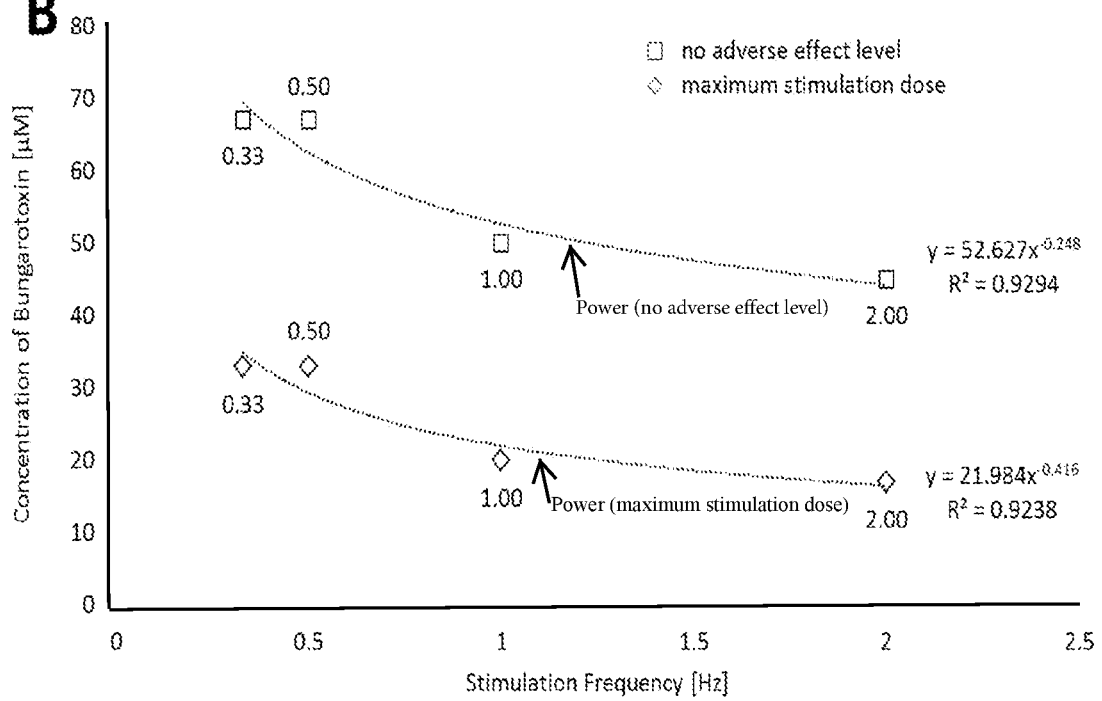

Low concentrations of bungarotoxin had a small excitatory effect, before the onset of inhibitory by higher concentrations. According to the fitted dose-response curves, the hermetic zone was frequency-dependent, as shown in FIG. 10B. The concentration of bungarotoxin that produced the highest excitatory effect is called the maximum stimulation dose. And the concentration where the excitatory effect diminishes to baseline is called the no adverse effect level. Both points shifted based on frequency of stimulation which could give information on the affinity of the bungarotoxin binding site.

In both these examples, a drug was added to disrupt the normal biochemical pathway involved in motoneuron signaling of skeletal muscle to contract by neuromuscular junction mediation. This caused the contractile response to change. In the case of curare, the drug was inhibitory based on concentration, however by applying a stimulation pattern of increased pulse frequency, the inhibition was revealed to be biphasic. This suggests there are two binding sites for curare with different affinities. In the case of bungarotoxin, there was an excitatory effect at lower concentrations followed by an inhibitory effect at higher concentrations. By applying a stimulation pattern of increased pulse frequency, both effects occur at a lower concentration which may give some indication about how the toxin is affecting the pathway. These examples were for the single neuromuscular junction module with a microtunnel array. It should be understood that the systems and methods described herein allow multiple modules to model other complex systems. Operation would follow the same scheme where a compound is added to disrupt the target pathway and stimulation patterns are applied to gain information about how the pathway was affected.

In some examples, the stimulus (for example, the drug, toxin, or metabolite) can be repeated over the course of a lengthy period of time, for example, to study chronic conditions. For example, the drug, toxin or metabolite could be applied repeatedly over the course of 28 days or more. In some examples, the drug, toxin, or metabolite might be spaced by a certain time duration. For example, a repeated stimulus might be spaced from the last stimulus by at least 24 hours.

Example 7

Multivariate Analysis. This system can allow the stimulation waveform and/or drug, toxin, or metabolite concentration to vary. Further, the number of modules and fluidic interconnects can vary. The functional readout of a target module can then be recorded under all or some of those various conditions. Multivariate analysis can be applied to the functional readouts to map them back to biochemical pathways. The resulting output will be a unique signature of how the pathway is being manipulated. This includes unique dose-response curves that contain frequency dependent features such as biphasic and hermetic regions.

As described herein, a micro cell culture analog device can include a plurality of components, where each component includes a cell culture of a different cell type. For example, a micro cell culture analog device can include a first component having a first chamber and including a cell culture of a first cell type (e.g., liver), a second component having a second chamber and including a cell culture of a second cell type (e.g., kidney), and a third component having a third chamber and including a cell culture of a third cell type (e.g., other than liver or kidney), etc. It should be understood that the number of components and/or the types of cell cultures included in each of the components is not intended to be limited by the examples.

Optionally, as described herein, respective stimulation electrodes can be arranged in one or more of the components. Optionally, in some implementations, respective stimulation electrodes are arranged in each of the components. Alternatively, in some implementations, respective stimulation electrodes are arranged in select components (but less than all of the components). The respective stimulation electrodes can be operably connected to a stimulus generator (e.g., stimulus generator 103 of FIG. 1). As described herein, the stimulus generator can be configured to apply a stimulus signal to the respective stimulation electrodes, which can electrically stimulate the components, where each component includes a different cell culture. This disclosure contemplates that the stimulus signal can be applied before, during, and/or after a drug, toxin, and/or metabolite has been introduced to the micro cell analog device. Additionally, as described herein, electrical stimulation parameters can be varied to gain information about how a stimulus affects different cell types.

Alternatively or additionally, a component may include a sensor equipped to respond to or detect a functional readout from a cell culture, such as force, frequency of action potential, or amplitude of action potential. Sensors such as microcantilever arrays can detect changes in cell force, for example, whereas sensors such as microelectrode arrays can detect changes in electrical activity of a cell culture. A component can also include a recording device (e.g., laser/photodetector, image capturing device, and/or computer, etc.) operably connected to one or more of the components and, in some cases, to the sensor. Optionally, in some implementations, a recording device can be configured to record cell responses from the cell cultures included in each of the components. Alternatively, in some implementations, a recording device can be configured to record cell response from the cell cultures included in select components (but less than all of the components). This disclosure contemplates that the respective cell responses of the cell cultures included in each of the components can be recorded, for example, before, during, and/or after a drug, toxin, and/or metabolite has been introduced to the micro cell culture analog device. For example, in the example above, respective cell responses of liver, kidney, and other than liver or kidney cells can be recorded from the first, second, and third components of the micro cell culture analog device.

Figure 11:
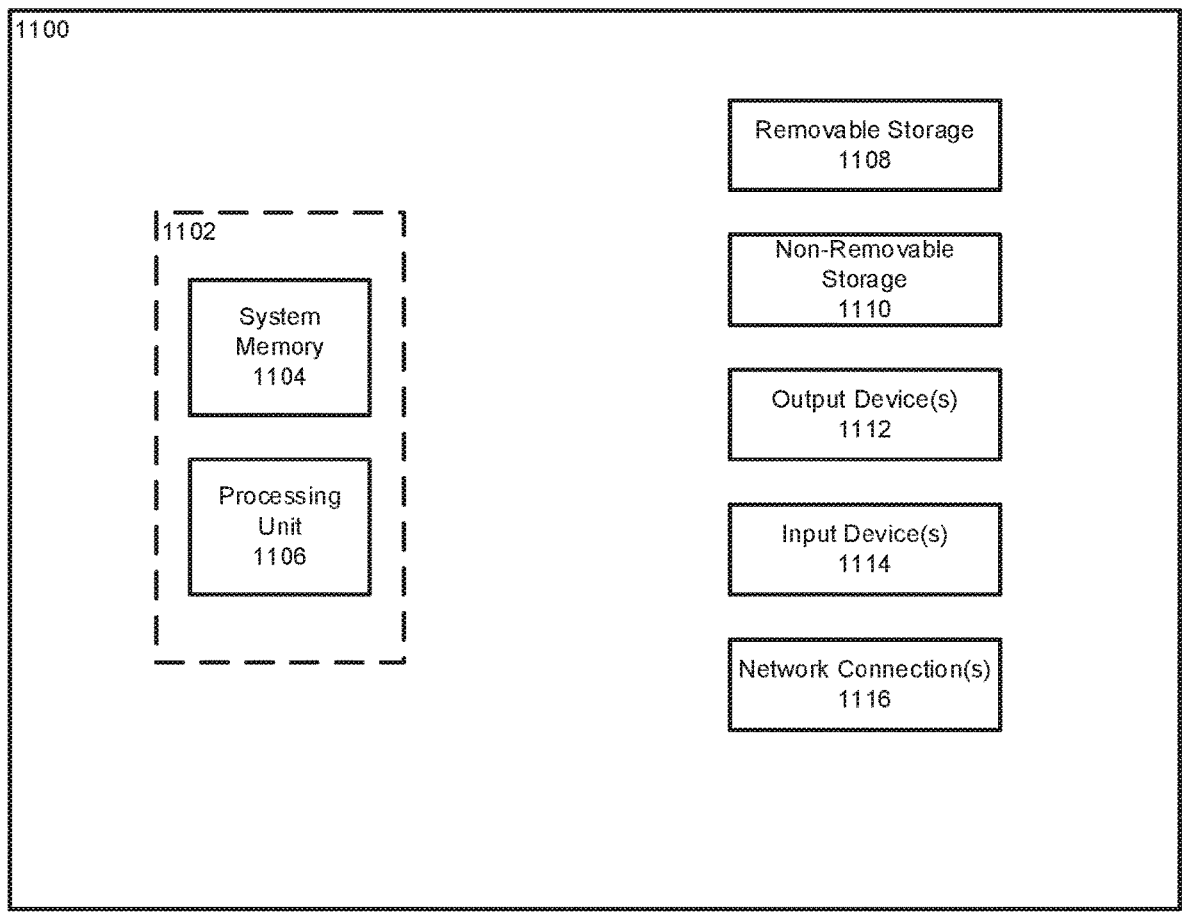
FIG. 11 is an example computing device.

The respective cell responses can be stored in memory of a computing device (e.g., computing device 1100 of FIG. 11). Optionally, respective cell responses can be stored in a database or other data structure. For example, a drug, toxin, and/or metabolite can be introduced to a micro cell culture analog device. The respective cell responses of the cell cultures included in each of the components to drug, toxin, and/or metabolite can be recorded and stored. Optionally, electrical stimulation can be applied in the presence of the drug, toxin, and/or metabolite. Characteristics (e.g., frequency, amplitude, etc.) of the electrical stimulation can, in some cases, be varied in the presence of the drug, toxin, and/or metabolite, and the respective cell responses from each of the components to the electrical stimulation can be recorded and stored. This disclosure contemplates that the process of electrical stimulation and recording/storage can be performed when the micro cell culture analog device is exposed to each of a plurality of drugs, toxin, and/or metabolites. Additional data on how the cells react to the drug, toxin, metabolite and/or electrical stimulation can also be recorded. For example, the exposure to a drug may alter the protein or RNA signature of a cell. As such, the concentration of biomarkers excreted or expressed internally by the cells may also be recorded and stored as cellular responses. Biomarkers can include, for example, small molecules, hormones, nucleic acids, RNA, peptides, proteins, gene products, or enzymes. All of the stored responses can later be analyzed for possible linkages to various cellular pathways. As described herein, the functional readouts from the various components obtained after exposure to the various perturbations (drug, toxin, and/or metabolite concentration and/or electrical stimulation) can be used to determine biochemical pathway information. Accordingly, this disclosure also contemplates that a multivariate analysis can be performed to determine the correlation between the functional readouts and the biochemical pathways within the cell or between cells. The multivariate analyses may be used to uncover new information on how an unknown drug, toxin, or metabolite acts on a biochemical pathway or to discover new biochemical pathways.

When determining pathway information, it is helpful to monitor more than just the functional output of the cell. That's because different drugs/toxins/metabolites with very different mechanisms of action can end up producing the same functional output. For example, a drug could interfere with the contractile apparatus in a muscle cell while another drug interferes with the transmission of nerve impulses to the muscle. Both manifest as a reduction in muscle contractile force under functional readout. To pinpoint how a drug is acting, more information is needed. The disclosed cell culture analog system provides that capability by allowing the functional output to be measured under many conditions. The test compound concentration and electrical stimulation waveform can be varied as in Examples 5 and 6. The modularity feature allows the number and type of components to vary as well as the flow. For example, a liver module can provide first-pass drug metabolism by proper flow routing, and liver metabolites may have a different effect on the muscle cell culture than the drug itself. Varying multiple conditions in an experiment not only generates functional output that is more likely to be unique, each condition gives hints as to where along the biochemical pathway a test compound is acting. For the prior muscle example, stimulating the muscle directly compared to stimulating the neurons would give information on whether the drug acted on the contractile apparatus or nerve transmission. Each test condition affects the cells differently and generates a new functional output. The variations in test conditions and results can be stored in the database and plugged into the multivariate analysis to lead back to the pathway information, which can then also be stored in the database and compared to or used in the analysis of future experiments. The database may also contain information about how known drugs, toxins, metabolites, electrical stimuli, or other types of stimuli affect particular biochemical pathways. This data pertaining to known stimuli may be used as an aid in multivariate analyses to determine how biochemical pathways are affected by new stimuli that is less understood.

Example Computing Device

It should be appreciated that the logical operations described herein with respect to the various figures may be implemented (1) as a sequence of computer implemented acts or program modules (i.e., software) running on a computing device (e.g., the computing device described in FIG. 11), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Referring to FIG. 11, an example computing device 1100 upon which embodiments of the invention may be implemented is illustrated. It should be understood that the example computing device 1100 is only one example of a suitable computing environment upon which embodiments of the invention may be implemented. Optionally, the computing device 1100 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 1100 typically includes at least one processing unit 1106 and system memory 1104. Depending on the exact configuration and type of computing device, system memory 1104 may be volatile (such as random access memory (RAM)), non-volatile (such as read-only memory (ROM), flash memory, etc.), or some combination of the two. This most basic configuration is illustrated in FIG. 11 by dashed line 1102. The processing unit 1106 may be a standard programmable processor that performs arithmetic and logic operations necessary for operation of the computing device 1100. The computing device 1100 may also include a bus or other communication mechanism for communicating information among various components of the computing device 1100.

Computing device 1100 may have additional features/functionality. For example, computing device 1100 may include additional storage such as removable storage 1108 and non-removable storage 1110 including, but not limited to, magnetic or optical disks or tapes. Computing device 1100 may also contain network connection(s) 1116 that allow the device to communicate with other devices. Computing device 1100 may also have input device(s) 1114 such as a keyboard, mouse, touch screen, etc. Output device(s) 1112 such as a display, speakers, printer, etc. may also be included. The additional devices may be connected to the bus in order to facilitate communication of data among the components of the computing device 1100. All these devices are well known in the art and need not be discussed at length here.

The processing unit 1106 may be configured to execute program code encoded in tangible, computer-readable media. Tangible, computer-readable media refers to any media that is capable of providing data that causes the computing device 1100 (i.e., a machine) to operate in a particular fashion. Various computer-readable media may be utilized to provide instructions to the processing unit 1106 for execution. Example tangible, computer-readable media may include, but is not limited to, volatile media, non-volatile media, removable media and non-removable media implemented in any method or technology for storage of information such as computer readable instructions, data structures, program modules or other data. System memory 1104, removable storage 1108, and non-removable storage 1110 are all examples of tangible, computer storage media.

Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 1106 may execute program code stored in the system memory 1104. For example, the bus may carry data to the system memory 1104, from which the processing unit 1106 receives and executes instructions. The data received by the system memory 1104 may optionally be stored on the removable storage 1108 or the non-removable storage 1110 before or after execution by the processing unit 1106.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

REFERENCES

1. Agarwal A, et al. Microfluidic heart on a chip for higher throughput pharmacological studies. Lab on a chip, d (2013).
2. Ali H H, Utting J E, Gray C. Stimulus frequency in the detection of neuromuscular block in humans. Br J Anaesth 1970; 42:967-78.
3. Bellas E, et al. In vitro 3D full-thickness skin-equivalent tissue model using silk and collagen biomaterials. Macromolecular bioscience 12, 1627-1636 (2012).
4. Bers D M. Cardiac excitation-contraction coupling. Nature 2002; 415(6868): 198-205.
5. Carlsson L. In vitro and in vivo models for testing arrhythmogenesis in drugs. Journal of Internal Medicine 2006; 259(1): 70-80.

6. Dakhel Y, et al. Erythomycin potentiates pr interval prolonging effect of verapamil in the rat: A pharmacodynamic drug interaction. Toxicol Appl Phamacol 2006; 214: 24-29.
7. Das M, et al. A defined long-term in vitro tissue engineered model of neuromuscular junctions. Biomaterials 2010; 31: 4880-4888.
8. Das M, et al. Differentiation of skeletal muscle and integration of myotubes with silicon microstructures using serum-free medium and a synthetic silane substrate. Nature Protocols 2007: 2(7): 1795-1801.
9. Das M. et al. Embryonic motor neuron-skeletal muscle co-culture in a defined system. Neuroscience 2007; 146: 481-488
10. Das M, et al. Long-term culture of embyonic rat cardiomyocytes on an organosilane surface in a serum free medium. Biomaterials 2004; 25(25): 5643-5647.
11. Das M, et al. Skeletal muscle tissue engineering: A maturation model promoting long-term survival of myotubes, structural development of the excitation-contraction coupling apparatus and neonatal mvosin heavy chain expression. Biomaterials 30, 5392-5402 (2009).
12. Das M. et al. Skeletal muscle tissue engineering: An improved model promoting long term survival of myotubes, structural development of e-c coupling apparatus and neonatal myosin heavy chain (mhc) expression. Biomaterials 2009; 30: 5392-5402.
13. Das M, et al. Temporal neurotransmitter conditioning restores the functional activity of adult spinal cord neurons in long-term culture. Experimental Neurology 2008; 209: 171-180
14. Das M, et al. A defined long-term in vitro tissue engineered model of neuromuscular junctions. Biomaterials 31, 4880-4888 (2010).
15. Das, M. et al. A defined system to allow skeletal muscle differentiation and subsequent integration with silicon microstructures. Biomaterials 27, 4374-4380 (2006).
16. Das M. et al. Electrophysiological and morphological characterization of rat embryonic motoneurons in a defined system. Biotechnology progress 19, 1756-1761, (2003).
17. Davis, H. et al. Rat Cortical Oligodendrocyte-Embryonic Motoneuron Co-Culture; An Axon-Oligodendrocyte Interaction Model. Journal biomaterials tissue engine 2, 206-214 (2012).
18. Dhir V, et al. Patterning of diverse mammalian cell types in serum free medium with photoablation. Biotechnol Prog 2009: 25(2): 594-603.
19. Edwards D, et al. Addition of glutamate to serum-free culture promotes recovery of electrical activity in adult hippocampal neurons in vitro. J Neuroscience meth 190, 155-163 (2010).
20. Guo X F. et al. Characterization of a human fetal spinal cord stem cell line nsi-566rsc and its induction to functional motoneurons. Tissue Engineering and Regenerative Medicine 2010; 4: 181-193.
21. Guo X F, et al. Nmj formation between human stem cell derived motoneurons and rat skeletal muscle in a defined system. Tissue Engineering: Part C 2010; 16(6): 1347-1355.
22. Guo X, et al. Neuromuscular junction formation between human stem cell-derived motoneurons and human skeletal muscle in a defined system. Biomaterials 32, 9602-9611 (2011).
23. Guo X, et al. Characterization of a human fetal spinal cord stem cell line, NSI-566RSC, and its induction to functional motoneurons. Journal of Tissue Engineering and Regenerative Medicine 4, 181-193 (2010).
24. Guo X, et al. Derivation of sensory neurons and neural crest stem cells from human neural progenitor hNP1. Biomaterials 34, 4418-4427 (2013).
25. Hughes B, 2007 fda drug approvals: A year of flux specialty products dominate innovative drug approvals—a trend that looks set to continue. Nature Reviews Drug Discovery 2008; 7: 107-109.
26. Huh, D. et al. Reconstituting organ-level lung functions on a chip. Science 328, 1662-1668 (2010).
27. Jung D R, et al. Cell-based sensor microelectrode array characterized by imaging x-ray photoelectron spectroscopy, scanning electron microscopy, impedance measurements, and extracellular recordings. J VacSciTechnol A 1998: 16(3): 1183-1188.
28. Kang J H, et al. In vitro 3D model for human vascularized adipose tissue. Tissue Eng Part A 15, 2227-2236 (2009).
29. Kim C. et al. Non-cardiomyocytes influence the electrophysiological maturation of human embryonic stem cell-derived cardiomyocytes during differentiation. Stem cells and development 2010: 19(6): 783-795.
30. Kita-Matsuo H, et al. Lentiviral vectors and protocols for creation of stable hesc lines for fluorescent tracking and drug resistance selection of cardiomyocytes. PLoS ONE 2009: 4(4): e5046.
31. Lawrence C L, et al. Nonclinical proarrhythmia models: Predicting torsades de pointes. Journal of Pharmacological and Toxicological Methods 2005; 52(1): 46-59.
32. Lipsett M A, et al. Acinar plasticity: development of a novel in vitro model to study human acinar-to-duct-to-islet differentiation. Pancreas 34, 452-457 (2007).
33. Liu W P, et al. Enantioselectivity in environmental safety of current chiral insecticides. Proc Natl Acad Sci USA 2005; 102(3): 701-706.
34. Lund A E, et al. Dose-dependent interaction of the pyrethroid isomers with sodium-channels of squid axon-membranes. Neurotoxicology 1982; 3(1): 11-24.
35. Maduell F. Hemodiafiltration. Hemodial Int 2005; 9(1): 47-55.
36. Mahler G J, et al. Characterization of a gastrointestinal tract microscale cell culture analog used to predict drug toxicity. Biotechnol Bioeng 2009; 104(1): 193-205.
37. Mahler G J, et al. Characterization of caco-2 and ht29-mtx co-cultures in an in vitro digestion/cell culture model used to predict iron bioavailability. J Nutr Biochem 2009; 20(7): 494-502.
38. Marona H R N, et al. Determination of sparfloxcin and its degradation products by hplc-pda. J Antimicrob Chemother 1999: 44: 301-302.
39. McAuliffe G J, et al. Development of a gastrointestinal tract microscale cell culture analog to predict drug transport. Mol Cell Bioengr 2008; 5(2): 119-132.
40. Meyer T, et al. Qt-screen: High-throughput cardiac safety pharmacology by extracellular electrophysiology on primary cardiac myocytes. Assay and Drug Development Technologies 2004: 2(5): 507-514.
41. Mohan D K, et al. Toxin detection based on action potential shape analysis using a realistic mathematical model of differentiated ng108-15 cells. Biosens Bioelectron 2006; 21: 1804-1811.
42. Molnar P, et al. Photolithographic patterning of c2c12 myotubes using vitronectin as growth substrate in serum-free medium. Biotechnol Prog 2007; 23(1): 265-268.

43. Molnar P, et al. Synaptic connectivity in engineered neuronal networks, in Patch-clamp methods and protocols, Molnar P and Hickman J J. Editors, 2007, Humana Press: New York.
44. Mufti N A, et al. Different in vitro systems affect cyp1a1 activity in response to 2,3,7,8-tetrachlorodibenzo-p-dioxin. Toxicol in vitro 1998: 12: 259-272.
45. Nakamura Y, et al. The in vitro metabolism of a pyrethroid insecticide, permethrin, and its hydrolysis products in rats. Toxicol Appl Pharmacol 2007: 235: 176-184.
46. Natarajan A. et al. Engineered In Vitro Feed-Forward Networks. J Biotechnol Biomater 3, 2 (2013).
47. Natarajan A, et al. Multielectrode recordings of cardiac action potentials as a high throughput method to evaluate pesticide toxicity. Toxicol In Vitro 2006; 20(3): 375-381.
48. Natarajan A, et al. Patterned cardiomyocytes on microelectrode arrays as a functional, high information content drug screening platform. Biomaterials 2011: in press.
49. Natarajan, A. et al. Patterned cardiomyocytes on microelectrode arrays as a functional, high information content drug screening platform. Biomaterials 32, 4267-4274 (2011).
50. Oh T-i, et al. Real-time fluorescence detection of multiple microscale cell culture analog devices in situ. Cytometry Part A 2007; 71A: 857-865.
51. Pointer C, P et al. Ht29-mtx and caco-21tc7 monolayers as predictive models for human intestinal absorption: Role of mucus layer. J Pharm Sci 2001; 90: 1608-1619.
52. Rumsey J W. et al. Node of ranvier formation on motoneurons in vitro. Biomaterials 2009: 30: 3567-3572.
53. Rumsey J W, et al. Tissue engineering the mechanosensory circuit of the stretch reflex arc: Sensory neuron innervation of intrafusal muscle fibers. Biomaterials 31, 8218-8227 (2010).
54. Schaffner A E, et al. Investigation of the factors necessary for growth of hippocampal neurons in a defined system. J Neurosci Methods 1995; 62(1-2): 111-9.
55. Schaffner A E, et al. Investigation of the factors necessary for growth of hippocampal neurons in a defined system. Journal of neuroscience methods 62, 111-119 (1995).
56. Scollon E J, et al. In vitro metabolism of pyrethroid pesticides by rat and human hepatic microsomes and cytochrome p450 isoforms. Drug Metabolism and Disposition 2009; 37(1): 221-228.
57. Selivanova O M, et al. Compact globular structure of thermos *Thermophilus* ribosomal protein sl in solution. J Biol Chem 2003; 278(38): 36311-36314.
58. Sin A. et al. The design and fabrication of three-chamber microscale cell culture analog devices with integrated dissolved oxygen sensors. Biotechnol Prog 2004: 20: 338-345.
59. Subramanian, B. et al. Tissue-engineered three-dimensional in vitro models for normal and diseased kidney. Tissue Eng Part A 16, 2821-2831 (2010).
60. Sung J H, et al. A micro cell culture analog with 3-d hydrogel culture of multiple cell lines to assess metabolism-dependent cytotoxicity of anti-cancer drugs. Lab Chip 2009; 9(10): 1385-1394.
61. Sung J H, et al. A microfluidic device for a pharmacokinetic-pharmacodynamic (pk-pd) model on a chip. Lab Chip 2010; 10: 446-455.
62. Sung J H, et al. Fluorescence optical detection in situ for real time monitoring of enzymatic activity of liver cells in multiple microfludic devices. Biotechnol Bioeng 2009: 104: 516-525.
63. Sung J H, et al. Prevention of air bubble formation in a microfluidic perfusion cell culture system using a microscale bubble trap. Biomed Microdevices 2009: 11: 731-738.
64. Sung J H, et al. Microfabricated mammalian organ systems and their integration into models of whole animals and humans. Lab on a chip 13, 1201-1212 (2013).
65. Suter W. Predictive value of in vitro safety studies. Current Opinion in Chemical Biology 2006; 10(4): 362-366.
66. Sutton N M, et al Clinical effects and outcome of feline permethrin spot-on poisonings reported to the veterinary poisons information service (vpis), london. J Feline Med & Surgery 2007: 9: 335-339.
67. Swvnghedauw B. Molecular mechanisms of myocardial remodeling. Physiol Rev 1999; 79(1): 215-262.
68. Takagishi Y, et al. Species-specific difference in distribution of voltage-gated l-type ca2+ channels of cardiac myocytes. Am J Physiol Cell Physiol 2000; 279(6): C1963-1969.
69. Tatosian D A, et al. A novel system for evaluation of drug mixtures for potential efficacy in treating multidrug resistant cancers. Biotechnol Bioeng 2009; 103(1): 187-198.
70. van der Valk J, et al. Optimization of chemically defined cell culture media-replacing fetal bovine serum in mammalian in vitro methods. Toxicology in vitro: an international journal published in association with BIBRA 24, 1053-1063 (2010).
71. Varghese K, et al. A new target for amyloid beta toxicity validated by standard and high-throughput electrophysiology. PLoS One 2010: 5(1): e8643.
72. Varghese K et al. Regeneration and characterization of adult mouse hippocampal neurons in a defined in vitro system. J Neurosci Methods 2009: 177: 51-59.
73. Viravaidva K, et al. Incorporation of 3t3-l1 cells to mimic bioaccumulation in a microscale cell culture analog device for toxicity studies. Biotechnol Prog 2004; 20: 590-597.
74. Wagner 1, et al. A dynamic multi-organ-chip for long-term cultivation and substance testing proven by 3D human liver and skin tissue co-culture. Lab on a chip (2013).
75. Wilson K, et al. Direct patterning of coplanar polyethylene glycol alkylsilane monolayers by deep-ultraviolet photolithography as a general method for high fidelity, long-term cell patterning and culture. JUST B 2011; in press.
76. Wilson K, et al. Integration of functional myotubes with a bio-mems device for non-invasive interrogation. Lab Chip 2007; 7: 920-922.
77. Wilson K, et al. Measurement of contractile stress generated by cultured muscle on silicon cantilevers. PLoS One 2010: 5(6): el11042.
78. Xu H, et al. Development of a stable dual cell-line gfp expression system to study estrogenic endocrine disruptors. Biotechnol Bioeng 2008; 101(6): 1276-1287.
79. Zimmermann W H, et al. Tissue engineering of a differentiated cardiac muscle construct. Circulation Research 2002; 90(2): 223-230.

What is claimed is:
1. A cell culture analog system for simulating the physiological condition of a living subject comprising:
a first chamber comprising a first type of cell,
a second chamber in fluid connection with the first chamber, the second chamber comprising a second type of cell, a first sensor for non-invasively measuring a function of the first type of cell,
a second sensor for non-invasively measuring a function of the second type of cell, and
a computing device operably connected to the first sensor and the second sensor, wherein the computing device is configured to:
receive data from at least one of the first sensor and the second sensor, the data comprising the function of at least one of the first type or the second type of cell, and
apply a multivariate analysis to the data, wherein the multivariate analysis draws correlations between the data and biochemical pathways within the first type of cell, the second type of cell, or both,
wherein the first chamber, the second chamber, the first sensor, and the second sensor are arranged on a chip in a planar sequential relationship.

2. The cell culture analog system of claim 1, wherein the computing device is configured to access a database, wherein the database comprises information about how a stimulus affects biochemical pathways within the first type of cell, the second type of cell, or both.

3. The cell culture analog system of claim 2, wherein the computing device is configured to store the data to the database, recover a first set of data from the database for comparison to a second set of data, or both.

4. The cell culture analog system of claim 1, wherein the data comprises one or more of the frequency of a cellular action potential, the amplitude of a cellular action potential, a cellular contractile force, and a concentration of a biomarker.

5. The cell culture analog system of claim 1, further comprising a third cell type, wherein each of the first, second, and third cell types are selected from the group consisting of: cardiomyocytes, myotubes, liver cells, kidney cells, neurons, epithelial cells, and mucus-producing cells.

6. The cell culture analog system of claim 1, wherein each of the first and second sensors is selected from the group consisting of: a microcantilever, a microelectrode array (MEA), and a light sensor.

7. The cell culture analog system of claim 1, further comprising a third type of cell, wherein the third type of cell is a liver cell or a kidney cell.

8. The cell culture analog system of claim 1, wherein the first type of cell is a muscle cell or neuron.

9. The cell culture analog system of claim 1, further comprising a neuron forming a neuromuscular junction with the first cell type.

10. The cell culture analog system of claim 1, further comprising a muscle-simulating component, the muscle-simulating component comprising one or more microcantilevers having cardiomyocytes or myotubes cultured thereon.

11. The cell culture analog system of claim 10, wherein the muscle-simulating component further comprises a microelectrode array having neurons cultured thereon.

12. The cell culture analog system of claim 1, further comprising a stimulus generator operably connected to stimulation electrodes, wherein the stimulation electrodes are in electrical contact with the at least one of the first type of cell or the second type of cell, and wherein the stimulus generator is configured to apply a stimulus signal to the stimulation electrodes.

13. The cell culture analog system of claim 12, wherein the computing device is operably connected to the stimulus generator and configured to vary a characteristic of the stimulus signal.

14. The cell culture analog system of claim 1, further comprising a recording device operably connected to the computing device and at least one of the first sensor or the second sensor, wherein the recording device is configured to record data from at least one of the first sensor and the second sensor.

15. The cell culture analog system of claim 14, wherein the computing device is further configured to receive a timing signal from a stimulus generator, wherein operations of the stimulus generator and the recording device are synchronized based on the timing signal.

16. A cell culture analog system for simulating the physiological condition of a living subject comprising:
a first chamber comprising a first type of cell,
a second chamber in fluid connection with the first chamber, the second chamber comprising a second type of cell,
a first sensor for non-invasively measuring a function of the first type of cell,
a second sensor for non-invasively measuring a function of the second type of cell,
a stimulus generator operably connected to stimulation electrodes, wherein the stimulation electrodes are in electrical contact with the at least one of the first type of cell or the second type of cell, and wherein the stimulus generator is configured to apply a stimulus signal to the stimulation electrodes, and
a computing device operably connected to the first sensor and the second sensor, wherein the computing device is configured to:
receive data from at least one of the first sensor and the second sensor, the data comprising the function of at least one of the first type or the second type of cell, and
apply a multivariate analysis to the data, wherein the multivariate analysis draws correlations between the data and biochemical pathways within the first type of cell, the second type of cell, or both.

17. The cell culture analog system of claim 16, wherein the computing device is configured to access a database, wherein the database comprises information about how a stimulus affects biochemical pathways within the first type of cell, the second type of cell, or both.

18. The cell culture analog system of claim 17, wherein the computing device is configured to store the data to the database, recover a first set of data from the database for comparison to a second set of data, or both.

19. The cell culture analog system of claim 16, wherein the data comprises one or more of the frequency of a cellular action potential, the amplitude of a cellular action potential, a cellular contractile force, and a concentration of a biomarker.

20. The cell culture analog system of claim 16, further comprising a third cell type, wherein each of the first, second, and third cell types are selected from the group consisting of: cardiomyocytes, myotubes, liver cells, kidney cells, neurons, epithelial cells, and mucus-producing cells.

21. The cell culture analog system of claim 16, wherein each of the first and second sensors is selected from the group consisting of: a microcantilever, a microelectrode array (MEA), and a light sensor.

22. The cell culture analog system of claim 16, further comprising a third type of cell, wherein the third type of cell is a liver cell or a kidney cell.

23. The cell culture analog system of claim 16, wherein the first type of cell is a muscle cell or neuron.

24. The cell culture analog system of claim 16, further comprising a neuron forming a neuromuscular junction with the first cell type.

25. The cell culture analog system of claim 16, further comprising a muscle-simulating component, the muscle-simulating component comprising one or more microcantilevers having cardiomyocytes or myotubes cultured thereon.

26. The cell culture analog system of claim 25, wherein the muscle-simulating component further comprises a microelectrode array having neurons cultured thereon.

27. The cell culture analog system of claim 16, wherein the first chamber, the second chamber, the first sensor, and the second sensor are arranged on a chip in a planar sequential relationship.

28. The cell culture analog system of claim 16, wherein the computing device is operably connected to the stimulus generator and configured to vary a characteristic of the stimulus signal.

29. The cell culture analog system of claim 16, further comprising a recording device operably connected to the computing device and at least one of the first sensor or the second sensor, wherein the recording device is configured to record data from at least one of the first sensor and the second sensor.

30. The cell culture analog system of claim 29, wherein the computing device is further configured to receive a timing signal from a stimulus generator, wherein operations of the stimulus generator and the recording device are synchronized based on the timing signal.

* * * * *